(12) United States Patent
Brænden et al.

(10) Patent No.: US 9,249,086 B2
(45) Date of Patent: Feb. 2, 2016

(54) CARBOXYLIC ACID ALA ESTERS

(71) Applicant: Photocure ASA, Oslo (NO)

(72) Inventors: Jon Erik Brænden, Oslo (NO); Colin Barry Charnock, Vestby (NO); Aslak Godal, Oslo (NO); Jo Klaveness, Oslo (NO); Nils Olav Nilsen, Oslo (NO)

(73) Assignee: Photocure ASA, Oslo (NO)

( * ) Notice: Subject to any disclaimer, the term of this patent is extended or adjusted under 35 U.S.C. 154(b) by 0 days.

(21) Appl. No.: 14/419,125

(22) PCT Filed: Aug. 2, 2013

(86) PCT No.: PCT/EP2013/066317
§ 371 (c)(1),
(2) Date: Feb. 2, 2015

(87) PCT Pub. No.: WO2014/020164
PCT Pub. Date: Feb. 6, 2014

(65) Prior Publication Data
US 2015/0191419 A1  Jul. 9, 2015

(30) Foreign Application Priority Data

Aug. 3, 2012 (EP) .................................... 12179277
Dec. 14, 2012 (EP) .................................... 12197305

(51) Int. Cl.
C07C 229/24 (2006.01)
A61K 41/00 (2006.01)
C07C 229/22 (2006.01)

(52) U.S. Cl.
CPC ........... *C07C 229/24* (2013.01); *A61K 41/0061* (2013.01); *C07C 229/22* (2013.01)

(58) Field of Classification Search
CPC . C07C 229/24; C07C 229/22; A61K 41/0061
See application file for complete search history.

(56) References Cited

U.S. PATENT DOCUMENTS

| | | | |
|---|---|---|---|
| 6,492,420 B2 | 12/2002 | Gierskcky et al. | |
| 6,905,671 B1 | 6/2005 | Tanaka et al. | |
| 7,135,162 B2 | 11/2006 | Tanaka et al. | |
| 7,287,646 B2 | 10/2007 | Gierskcky et al. | |
| 7,335,684 B2 | 2/2008 | Gierskcky et al. | |
| 7,563,819 B1 | 7/2009 | Klaveness et al. | |
| 7,888,526 B2 | 2/2011 | Braenden et al. | |
| 8,492,578 B2 * | 7/2013 | Glanzmann | A61K 8/44 560/155 |
| 2002/0183386 A1 | 12/2002 | Gierskcky et al. | |
| 2005/0031541 A1 | 2/2005 | Gierskcky et al. | |
| 2006/0018956 A1 | 1/2006 | Lee et al. | |
| 2010/0035754 A1 | 2/2010 | Watanabe et al. | |
| 2010/0173780 A1 | 7/2010 | Kondo et al. | |
| 2010/0203159 A1 | 8/2010 | Tachiya et al. | |
| 2010/0234231 A1 | 9/2010 | Takeuchi et al. | |
| 2010/0331183 A1 | 12/2010 | Takeuchi et al. | |
| 2011/0033386 A1 | 2/2011 | Inoue et al. | |
| 2011/0244110 A1 | 10/2011 | Tanaka et al. | |

FOREIGN PATENT DOCUMENTS

| | | |
|---|---|---|
| DE | 10312659 A1 | 10/2004 |
| EP | 2274979 A1 | 1/2011 |
| JP | H7188133 A | 7/1995 |
| JP | 2005314360 A | 11/2005 |
| JP | 2006182753 A | 7/2006 |
| WO | 9628412 A1 | 9/1996 |
| WO | 2006/051269 A1 | 5/2006 |
| WO | 2009/074811 A2 | 6/2009 |

OTHER PUBLICATIONS

Galande, Amit K. et al., "An Effective Method of On-Resin Disulfide Bond Formation in Peptides," Journal of Combinatorial Chemistry, 7(2), 174-177 CODEN; 2005.
Vallinayagam, Ramakrishnan et al., "Synthesis of novel and stable 5-aminolevulinic acid derivatives for the efficient synthsis of 5-aminolevulinic acid based prodrugs," Synthesis, (23), 3731-3735 CODEN: 2007.
International Preliminary Report on Patentability from PCT/EP2013/066317, mailed Feb. 3, 2015.

* cited by examiner

*Primary Examiner* — Shailendra Kumar
(74) *Attorney, Agent, or Firm* — Kenyon & Kenyon LLP

(57) ABSTRACT

The invention relates to new derivatives of 5-aminolevulinic acid (5-ALA) and their use as photosensitizing agents. In particular, it relates to compounds of general formula I and their pharmaceutically acceptable salts, to methods for preparing such compounds and their medical and cosmetic use, for example in methods of photodynamic therapy and diagnosis:

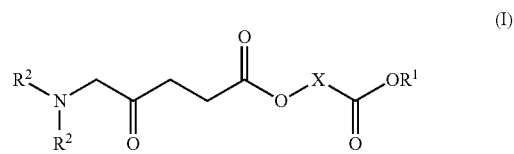

Figure 1:
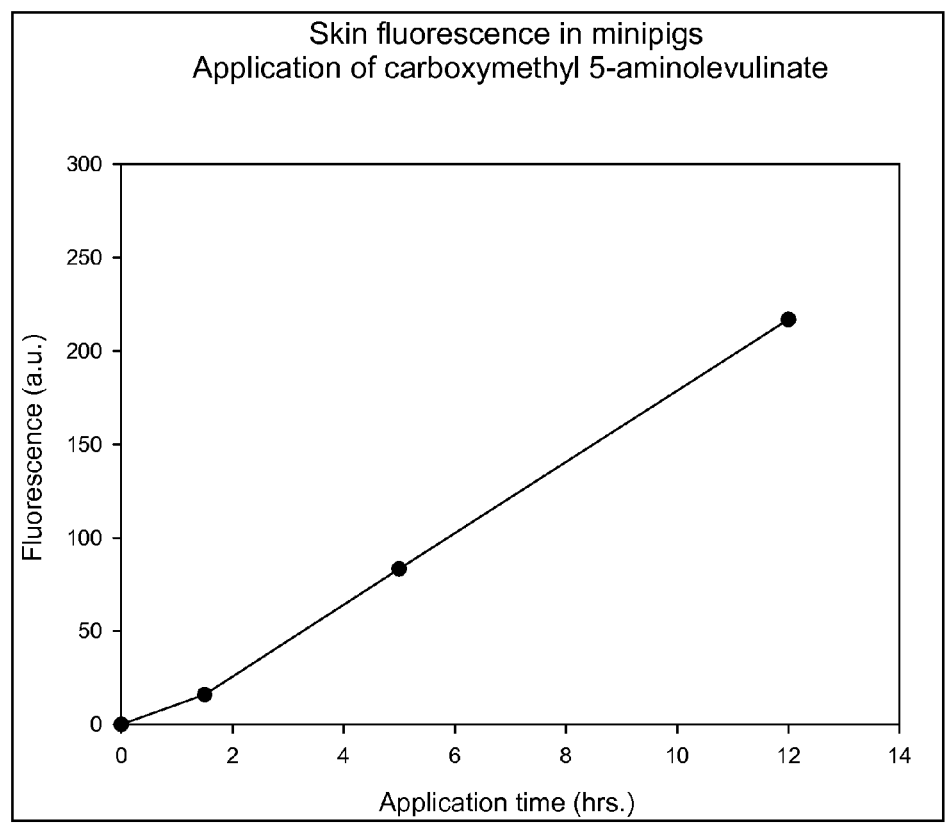

wherein
$R^1$ represents a hydrogen atom or an optionally substituted alkyl or cycloalkyl group;
$R^2$, each of which may be the same or different, represents a hydrogen atom or an optionally substituted alkyl group; and
X is a linking group.

19 Claims, 2 Drawing Sheets

CARBOXYLIC ACID ALA ESTERS

CROSS-REFERENCE TO RELATED APPLICATIONS

This application is a United States national phase of International Patent Application Serial No. PCT/EP2013/066317, filed on Aug. 2, 2013, which claims priority to European Patent Applications Nos. 12179277.4, filed Aug. 3, 2012, and 12197305.1, filed Dec. 14, 2012, the entire contents of which applications are incorporated herein by reference.

The present invention relates to novel derivatives of 5-aminolevulinic acid (5-ALA) and their use as photosensitising agents. In particular, it relates to compounds of general formula I and their pharmaceutically acceptable salts, to methods for preparing such compounds and their medical and cosmetic use, for example in methods of photodynamic therapy and diagnosis.

Photodynamic treatment (PDT) is a technique for the treatment of pre-cancerous lesions, cancer and non-cancerous diseases. PDT involves the administration of a photosensitiser or a precursor thereof (i.e. a "photosensitising agent") to an area of interest. The photosensitiser or precursor thereof is taken up into the cells, where a precursor of a photosensitiser is converted into a photosensitiser. Upon exposure of the area of interest to light, the photosensitiser is excited, usually from a ground singlet state to an excited singlet state. It then undergoes intersystem crossing to a longer-lived excited triplet state. One of the few chemical species present in tissue with a ground triplet state is molecular oxygen. When the photosensitiser and an oxygen molecule are in proximity, an energy transfer can take place that allows the photosensitiser to relax to its ground singlet state, and create an excited singlet state oxygen molecule. Singlet oxygen is a very aggressive chemical species and will very rapidly react with any nearby biomolecules. Ultimately, these destructive reactions will kill cells through apoptosis or necrosis, whereby for instance cancer cells are selectively killed. The mechanisms are still not fully understood, but studies suggest that the clinical result (i.e. the selectivity for cancerous cells) is not due to selective uptake by cancerous cells. Rather, there are similar levels of uptake in all cell types, but the processes of conversion and elimination are different in malignant cells and generally in metabolically active cells, such as inflamed or infected cells, leading to a concentration gradient between cancerous and normal tissue.

Several photosensitising agents are known and described in the literature, including 5-aminolevulinic acid (5-ALA) and certain derivatives thereof, e.g. 5-ALA esters, both of which are precursors of photosensitisers. These are converted intracellularly to protoporphyrins, such as protoporphyrin IX (PpIX), which are photosensitisers. Currently several pharmaceutical products comprising 5-ALA or an ester thereof are in clinical use for PDT and photodynamic diagnosis (PDD). One of them is Metvix®, a dermal product in the form of a cream comprising 5-ALA methyl ester (developed by Photocure ASA, Norway, and now sold by Galderma, Switzerland), for the photodynamic treatment of actinic keratosis and basal cell carcinoma. Another one is Levulan Kerastick® (DUSA Pharmaceuticals, Canada), a product for the photodynamic treatment of actinic keratosis which contains 5-ALA. Hexvix® (developed by Photocure ASA) is an aqueous solution which comprises 5-ALA hexyl ester for instillation into the bladder for diagnosis of bladder cancer.

However, a need still exists for alternative photosensitisers or precursors thereof. The present invention addresses this need by providing precursors of photosensitisers according to general formula I below.

Thus, viewed from a first aspect, the invention provides a compound of general formula I, or a pharmaceutically acceptable salt thereof:

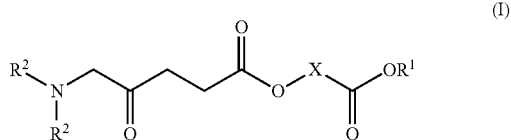

wherein
$R^1$ represents a hydrogen atom or an optionally substituted alkyl or cycloalkyl group;
$R^2$, each of which may be the same or different, represents a hydrogen atom or an optionally substituted alkyl group; and
X is a linking group.

In the compounds of formula I, it is preferred that the $-X-CO_2R^1$ portion is hydrophilic in nature. The term "hydrophilic" means that the $-X-CO_2R^1$ portion of the molecule has a tendency to interact with or be dissolved by water or other polar solvents and/or substances. The hydrophilic nature of this portion of the molecule may arise from the nature of group X and/or from the nature of the $-CO_2R^1$ group.

As such, either X may be hydrophilic, or the $-CO_2R^1$ group may be hydrophilic, or both X and the $-CO_2R^1$ group may be hydrophilic.

In a first embodiment, only the linking group X of the $-X-CO_2R^1$ portion of the compounds of general formula I is hydrophilic.

Typical examples of hydrophilic groups X are those which carry one or more substituents (i.e. pendant groups) that render the group hydrophilic, i.e. hydrophilic substituents. The term "hydrophilic substituent" denotes a substituent capable of hydrogen bonding. Typical and preferred hydrophilic substituents are hydroxyl, thiol, carboxyl, carbamoyl, ester and amine, more preferably hydroxyl, amine and thiol. Alternatively, hydrophilic groups X may contain one or more heteroatoms that render the group hydrophilic, i.e. heteroatoms capable of hydrogen bonding. Preferred heteroatoms are oxygen or sulphur.

Particular examples of hydrophilic groups X include alkylene groups interrupted by one or more heteroatoms, preferably by one or more oxygen atoms. Such groups include polyethylene glycol groups, preferably polyethylene glycol groups containing 1-4 ethylene oxide units. Other examples of hydrophilic groups X are alkylene groups, preferably $C_{1-4}$ alkylene groups, comprising one or more hydroxyl, thiol or amine substituents.

Where only X is hydrophilic, the group $R^1$ may be an optionally substituted alkyl group, i.e. straight-chained or branched alkyl group, or a cycloalkyl group. In the case where $R^1$ is substituted, this will be substituted by one or more non-hydrophilic substituents. The term "non-hydrophilic substituent" denotes a substituent which is essentially not capable of hydrogen bonding. Non-hydrophilic substituents do not include any of the groups mentioned herein as examples of hydrophilic groups, such as hydroxyl, thiol, carboxyl, carbamoyl, ester and amine. Preferred non-hydrophilic substituents are halo, preferably F or Cl, nitro and aryl. If the non-hydrophilic substituent is an aryl group, said aryl group may be substituted by one or more halo, alkyl, haloalkyl, alkoxy (e.g. $C_{1-3}$ alkoxy) or nitro groups.

In one embodiment, $R^1$ is an unsubstituted, straight-chained or branched alkyl group or an unsubstituted cycloalkyl group, preferably an unsubstituted, straight-chained alkyl group containing 4 to 20 carbon atoms (preferably 4 to 10 carbons, e.g. 4 to 8 carbons), an unsubstituted, branched alkyl group containing 4 to 20 carbon atoms (preferably 4 to 10 carbons, e.g. 4 to 8 carbons), or an unsubstituted cycloalkyl group containing 3 to 7 carbon atoms (preferably 3 to 6 carbon atoms).

If $R^1$ is an unsubstituted alkyl group, $R^1$ groups that are straight-chained alkyl groups are preferred. More preferred are $C_{4-10}$ straight-chained alkyl groups and most preferred are $C_{4-8}$ straight-chained alkyl groups. Representative examples of such groups are n-butyl, n-pentyl, n-hexyl, n-heptyl, n-octyl, n-nonly and n-decyl. Particularly preferred are n-butyl, n-pentyl, n-hexyl, n-heptyl and n-octyl.

If $R^1$ is an unsubstituted branched alkyl group, such branched alkyl groups preferably contain 4 to 20 carbon atoms, more preferably 4 to 10 carbon atoms and most preferably 4 to 8 carbon atoms. Representative examples of such branched alkyl groups include sec.-butyl, tert.-butyl, 2-methylbutyl, 3,3-dimethyl-1-butyl and 1-ethylbutyl. Preferred groups include sec.-butyl and tert.-butyl.

If $R^1$ is an unsubstituted cycloalkyl group, such cycloalkyl groups preferably consist of 3 to 6 carbon atoms, e.g. cyclopropyl, cyclobutyl, cyclopentyl or cyclohexyl.

If $R^1$ is a substituted alkyl group, this may be a straight-chained or branched alkyl or cycloalkyl group carrying one or more non-hydrophilic substituents, preferably one or two non-hydrophilic substituents. Where more than one non-hydrophilic substituent is present, these may be the same or different. Preferred non-hydrophilic substituents are halo, preferably F or Cl, nitro and aryl. If the non-hydrophilic substituent is an aryl group, said aryl group may be substituted by one or more halo, alkyl, haloalkyl, alkoxy (e.g. $C_{1-3}$ alkoxy) or nitro groups. Preferred such $R^1$ groups are $C_{1-2}$ alkyl substituted by one or more aryl groups, preferably one or two aryl groups which itself are optionally substituted by alkyl (e.g. $C_{1-4}$ alkyl), halo, nitro, haloalkyl or alkoxy (e.g. $C_{1-3}$ alkoxy). Examples of such $R^1$ groups include benzyl, 4-isopropylbenzyl, 4-methylbenzyl, 2-methylbenzyl, 3-methylbenzyl, 4-[t-butyl]benzyl, 4-[trifluoromethyl]benzyl, 4-methoxybenzyl, 3,4-[di-chloro]benzyl, 4-chlorobenzyl, 4-fluorobenzyl, 2-fluorobenzyl, 3-fluorobenzyl, 2,3,4,5,6-pentafluorobenzyl, 3-nitrobenzyl, 4-nitrobenzyl, 2-phenylethyl, 4-phenylbutyl and 4-diphenyl-methyl. More preferred such $R^1$ groups are benzyl, 4-isopropylbenzyl, 4-methylbenzyl, 4-nitrobenzyl and 4-chlorobenzyl. Most preferred is benzyl.

In a second embodiment, only the $—CO_2R^1$ group present in the $—X—CO_2R^1$ portion of the compounds of general formula I is a hydrophilic group. A typical and preferred example of such a group is $—CO_2H$, i.e. where $R^1$ represents a hydrogen atom. Alternative preferred examples are groups $—CO_2R^1$ wherein $R^1$ is a short straight-chain or branched alkyl group, preferably an alkyl group that contains 1-3 carbon atoms such as methyl, ethyl, n-propyl, and isopropyl.

In the second embodiment herein described, the linking group X is preferably a straight-chained or branched alkylene group, a cycloalkylene group, an arylene group or an aralkylene group which is optionally substituted by one or more non-hydrophilic substituents.

If X is a straight-chained alkylene group, this preferably consists of 1 to 16 carbon atoms, i.e. methylene, ethylene, propylene, butylene, pentylene, hexylene, heptylene, octylene, nonylene, decylene, undecylene, dodecylene, tridecylene, tetradecylene, pentadecylene or hexadecylene, more preferably 1 to 6 carbon atoms, i.e. methylene, ethylene, propylene, butylene, pentylene or hexylene, yet more preferably 1 to 4 carbon atoms, i.e. methylene, ethylene, propylene or butylene.

If X is a branched alkylene group, this preferably consists of 2 to 10 carbon atoms, more preferably of 2 to 6 carbon atoms. Preferred examples are methyl-methylene, dimethyl-methylene, 1-methyl-ethylene, 2-methyl-ethylene, 1,2-dimethylethylene, ethyl-methylene, isopropyl-methylene, 1-ethyl-ethylene and 2-ethyl-ethylene. Most preferred examples are methyl-methylene, ethyl-methylene and isopropyl-methylene.

If X is a cycloalkylene group, this preferably consists of 3 to 8 carbon atoms, more preferably of 5 or 6 carbon atoms. Preferred examples are cyclopentylene and cyclohexylene.

If X is an arylene group, this preferably consists of 6 to 12 carbon atoms. A preferred group is phenylene, i.e. $—C_6H_4—$, preferably with the free valencies at the carbon atoms 1 and 4.

If X is an aralkylene group, this preferably consists of 7 to 15 carbon atoms. A preferred group is benzylene, i.e. $—CH_2—C_6H_4—$, preferably with the free valency at the carbon atom 4 of the aromatic ring.

Any of the groups X described above, i.e. straight-chained or branched alkylene groups, cycloalkylene groups, arylene groups or aralkylene groups, may be optionally substituted by one or more non-hydrophilic substituents, e.g. by any of such groups herein described.

In a third embodiment of the invention, both X and the $—CO_2R^1$ group of the $—X—CO_2R^1$ portion of the compounds of general formula I are hydrophilic. Typical and preferred examples of such hydrophilic groups X and $—CO_2R^1$ are provided in the previous paragraphs above.

$R^2$, each of which may be the same or different, represents a hydrogen atom or an optionally substituted alkyl group (preferably a $C_{1-6}$ alkyl, e.g. a $C_{1-3}$ alkyl group). Where $R^2$ is an optionally substituted alkyl group, the substituents may be hydrophilic substituents or non-hydrophilic substituents as defined herein.

Preferred compounds according to the invention are those in which at least one $R^2$ represents a hydrogen atom. In a preferred embodiment, each $R^2$ represents a hydrogen atom.

In a preferred embodiment, the invention provides a compound of general formula I, or a pharmaceutically acceptable salt thereof, wherein
$R^1$ represents a hydrogen atom or a short, straight-chained or branched alkyl group, preferably a straight-chain or branched alkyl group that contains 1-3 carbon atoms such as methyl, ethyl, n-propyl or isopropyl;
$R^2$, each of which may be the same or different, represents a hydrogen atom or an optionally substituted alkyl group, preferably hydrogen; and the linking group X is
(a) an optionally substituted $C_{1-6}$ alkylene group, or
(b) an optionally substituted cycloalkylene, arylene or aralkylene group.

In a more preferred embodiment, the invention provides a compound of general formula I, or a pharmaceutically acceptable salt thereof, wherein
$R^1$ and $R^2$ each represent a hydrogen atom; and the linking group X is
(a) an optionally substituted $C_{1-6}$ alkylene group, or
(b) an optionally substituted cycloalkylene, arylene or aralkylene group.

In a more preferred embodiment, the invention provides a compound of general formula I, or a pharmaceutically acceptable salt thereof, wherein R¹ represents a hydrogen atom or a short straight-chain or branched alkyl group, preferably a straight-chain or branched alkyl group that contains 1-3 carbon atoms such as methyl, ethyl, n-propyl or isopropyl;

R², each of which may be the same or different, represents a hydrogen atom or an optionally substituted alkyl group, preferably hydrogen; and the linking group X is (a) an optionally substituted, straight-chained $C_{1-4}$ alkylene group or optionally substituted branched $C_{2-6}$ alkylene group, or (b) an optionally substituted $C_{5-6}$ cycloalkylene group, an optionally substituted $C_{6-12}$ arylene group, or an optionally substituted $C_{7-15}$ aralkylene group.

In a more preferred embodiment, the invention provides a compound of general formula I, or a pharmaceutically acceptable salt thereof, wherein R¹ and R² each represent a hydrogen atom; and the linking group X is (a) an optionally substituted, straight-chained $C_{1-4}$ alkylene group or optionally substituted, branched $C_{2-6}$ alkylene group, or (b) an optionally substituted $C_{5-6}$ cycloalkylene group, an optionally substituted $C_{6-12}$ arylene group, or an optionally substituted $C_{7-15}$ aralkylene group.

In one embodiment, such groups X may be unsubstituted. Alternatively, such groups may be substituted by one or more non-hydrophilic substituents as hereinbefore described. Where the linking group X is substituted, it may be substituted with one or more non-hydrophilic substituents. Where more than one substituent is present, these may be the same or different and may be attached to the same or different carbon atoms in the alkylene chain, cycloalkylene ring, arylene ring, or chain or ring of the aralkylene group.

In one embodiment the linking group X is an unsubstituted straight-chained $C_{1-6}$ alkylene group. Examples of such groups are an unsubstituted straight-chained $C_1$ alkylene group, i.e. a methylene group, an unsubstituted straight-chained $C_2$ alkylene group, i.e. an ethylene group, an unsubstituted straight-chained $C_3$ alkylene group, i.e. a propylene group, an unsubstituted straight-chained $C_4$ alkylene group, i.e. a butylene group, an unsubstituted straight-chained $C_5$ alkylene group, i.e. a pentylene group, and an unsubstituted straight-chained $C_6$ alkylene group, i.e. a hexylene group. Preferred linking groups X are unsubstituted straight-chained $C_{1-4}$ alkylene groups, i.e. methylene, ethylene, propylene and butylene.

In another embodiment, the linking group X is a substituted straight-chained $C_{1-6}$ alkylene group, preferably a substituted straight-chained $C_{1-4}$ alkylene group, more preferably a substituted $C_{1-2}$ alkylene group. Preferred substituents are halo, preferably F and Cl, and aryl. Where any substituent is an aryl group, the aryl may be unsubstituted or substituted by one or more halo, alkyl, haloalkyl, alkoxy (e.g. $C_{1-3}$ alkoxy) or nitro groups. In preferred embodiment, said aryl group is unsubstituted. One or more of such substituents (e.g. one or two) may be attached to the alkylene chain. Where more than one such substituent is present, these may be linked to the same carbon atom or to different carbon atoms present in the linking group X. In one embodiment, two halo substituents may be linked to the same carbon atom. Straight-chained $C_{1-6}$ alkylene groups, more preferably straight-chained $C_{1-4}$ alkylene groups, and even more preferably straight-chained $C_{1-2}$ alkylene groups which are mono- or di-fluorinated form a preferred aspect of the invention. Straight-chained $C_{1-6}$ alkylene groups, more preferably straight-chained $C_{1-4}$ alkylene groups, and even more preferably straight-chained $C_{1-2}$ alkylene groups which are substituted by an aryl substituent, preferably by phenyl, form another preferred aspect of the invention.

In yet another embodiment the linking group X is an unsubstituted branched $C_{2-6}$ alkylene group. Preferred examples of such groups X are methyl-methylene, i.e. —CH(CH₃)—, ethyl-methylene, i.e. —CH(CH₂CH₃)—, and isopropyl-methylene, i.e. —CH(CH—(CH₃)₂)—.

In yet another embodiment the linking group X is a substituted branched $C_{2-6}$ alkylene group. Preferred substituents are halo, preferably F and Cl and aryl. Where any substituent is any aryl group, said aryl may be unsubstituted or substituted by one or more halo, alkyl, haloalkyl, alkoxy (e.g. $C_{1-3}$ alkoxy) or nitro groups. In preferred embodiment, said aryl is unsubstituted. Halo is a preferred substituent and one or more of such substituents may be attached to the branched alkylene chain. Where more than one such substituent is present, these may be linked to the same carbon atom or to different carbon atoms present in the branched alkylene chain. A preferred example of such a group X is trifluoromethyl-methylene.

In yet another embodiment the linking group X is an unsubstituted cycloalkylene group such as cyclopropylene, cyclobutylene, cyclopentylene, cyclohexylene, cycloheptylene or cyclooctylene. Preferably the linking group X is an unsubstituted cycloalkylene group which consists of 5 or 6 carbon atoms, i.e. cyclopentylene or cyclohexylene.

In yet another embodiment the linking group X is an unsubstituted arylene group which consists of 6 or 12 carbon atoms. A preferred linking group X of this embodiment is phenylene, i.e. —C₆H₄—, preferably with the free valencies at the carbon atoms 1 and 4.

In yet another embodiment the linking group X is a substituted arylene group wherein the arylene group consists of 6 or 12 carbon atoms, preferably 6 carbon atoms. Preferred ring substituents are alkyl, halo and nitro. One or more of such substituents (e.g. one or two) may be attached to the arylene ring.

In yet another embodiment the linking group X is an unsubstituted aralkylene group which consists of 7 to 14 carbon atoms. A preferred linking group X of this embodiment is benzylene, i.e. —CH₂—C₆H₄—, preferably with the free valency at the carbon atom 4 of the aromatic ring.

Preferred examples of group X include —CH₂—, —CH₂CH₂—, —CH₂CH₂CH₂—, —CH(CH₃)—, —CF₂—, cyclohexylene, —CH₂—C₆H₄—, -phenylene-, and —CH(Ph)- (where Ph=phenyl).

Preferred compounds of the invention include those wherein X represents a group as described above and R¹ represents a hydrogen atom or a short straight-chain or branched alkyl group, preferably an alkyl group that contains 1-3 carbon atoms such as methyl, ethyl, n-propyl, and isopropyl, and each R² is the same and represents hydrogen.

Particular mention may be made of the following which represent preferred compounds according to the invention:

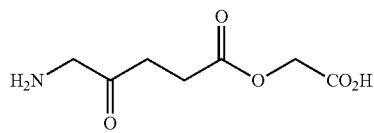

carboxymethyl 5-amino-4-oxopentanoate

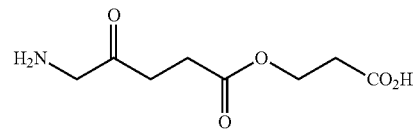

2-carboxyethyl 5-amino-4-oxopentanoate

-continued

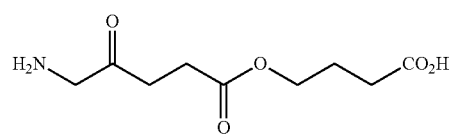
3-carboxypropyl 5-amino-4-oxopentanoate

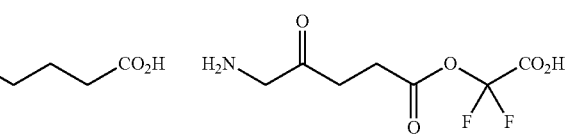
carboxydifluoromethyl 5-amino-4-oxopentanoate

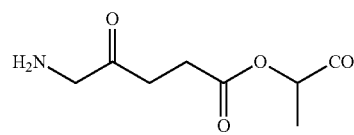
1-carboxyethyl 5-amino-4-oxopentanoate

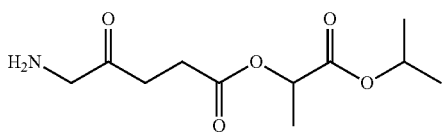
1-(isopropyl carboxy)ethyl 5-amino-4-oxopentanoate

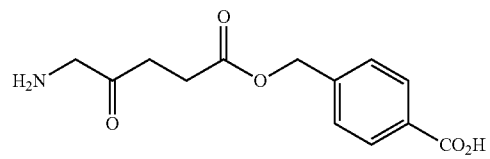
(4-carboxyphenyl)methyl 5-amino-4-oxopentanoate

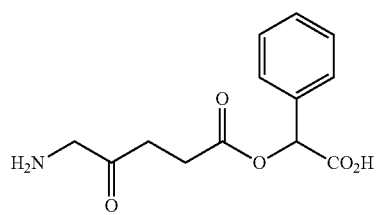
carboxyphenylmethyl 5-amino-4-oxopentanoate

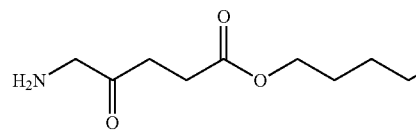
4-carboxybutyl 5-amino-4-oxopentanoate

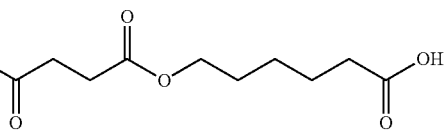
5-carboxypentyl 5-amino-4-oxopentanoate

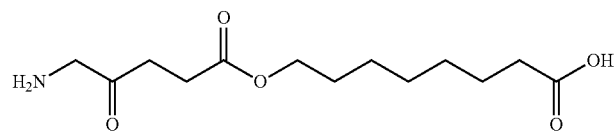
7-carboxyheptyl 5-amino-4-oxopentanoate

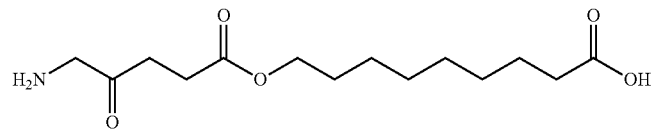
8-carboxyoctyl 5-amino-4-oxopentanoate

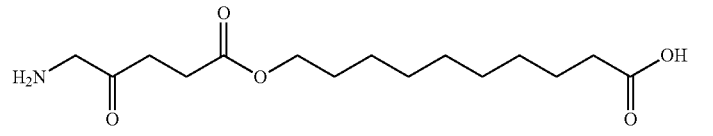
9-carboxynonyl 5-amino-4-oxopentanoate

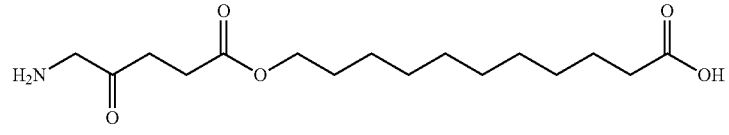
10-carboxydecyl 5-amino-4-oxopentanoate

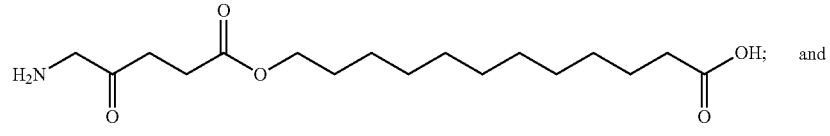
and 11-carboxyundecyl 5-amino-4-oxopentanoate

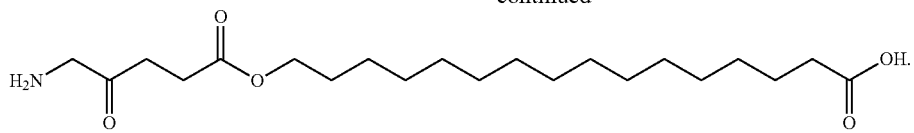

15-carboxypentadecyl 5-amino-4-oxopentanoate and their pharmaceutically acceptable salts.

As used herein, the term "alkyl", unless stated otherwise, refers to a saturated hydrocarbon group and is intended to cover any long or short chain, straight-chained and branched alkyl group.

As used herein, the term "alkylene" refers to a divalent radical derived from an alkane in which the free valencies form single bonds with the remainder of the molecule. The term includes straight-chained and branched alkylene groups.

As used herein, the term "cycloalkylene" refers to a divalent radical derived from a cycloalkane in which the free valencies form single bonds with the remainder of the molecule.

As used herein, the term "aryl" is intended to cover aromatic ring systems. Such ring systems may be monocyclic or polycyclic (e.g. bicyclic) and contain at least one unsaturated aromatic ring. Where these contain polycyclic rings, these may be fused.

The term "arylene" as used herein refers to a divalent radical derived from an aromatic hydrocarbon in which the free valencies form single bonds with the remainder of the molecule.

The term "aralkylene" as used herein refers to a divalent radical derived from an aryl-substituted alkyl or alkyl-substituted aryl with a single free valency both in the aryl and alkyl-part of the molecule in which the free valencies form single bonds with the remainder of the molecule.

Unless otherwise stated, the term "halo" or "halogen atom" includes fluoro, chloro, bromo and iodo.

The compounds of the invention may be provided in the form of a free amine, e.g. $-NH_2$, $-NHR^2$ or $-NR^2R^2$, or preferably in the form of a pharmaceutically acceptable salt. Such salts preferably are acid addition salts with pharmaceutically acceptable organic or inorganic acids.

Suitable acids include, for example, hydrochloric acid, nitric acid, hydrobromic acid, phosphoric acid, sulphuric acid, sulphonic acid and sulphonic acid derivatives, acetic acid, lactic acid, citric acid, tartaric acid, succinic acid, maleic acid, fumaric acid, ascorbic acid, oleic acid and stearic acid. Appropriate salts thus include, for example, hydrochloride, hydrobromide, nitrate, phosphate, sulphate, sulphonate, mesylate, tosylate, napsylate, acetate, lactate, citrate, tartrate, succinate, maleate, fumarate, ascorbate, oleate and stearate. Preferred acids are hydrochloric acid (HCl) and hydrobromic acid (HBr). Further preferred acids are nitric acid, sulphonic acid and sulphonic acid derivatives (e.g. methanesulphonic acid, naphthalenesulphonic acid or toluenesulphonic acid) as described in WO 2005/092838 to Photocure ASA, the entire contents of which are incorporated herein by reference.

The term "pharmaceutically acceptable salt" denotes a salt that is suitable for use in a pharmaceutical product and which fulfils the requirements related to for instance safety, bioavailability and tolerability (see for instance P. H. Stahl et al. (eds.) Handbook of Pharmaceutical Salts, Publisher Helvetica Chimica Acta, Zurich, 2002).

The compounds of the invention may be prepared using standard processes and procedures well-known in the art for derivatisation of multi-functional compounds, for example derivatisation of carboxylic acids. As known in the art, such reactions may involve protection and deprotection of appropriate groups such that only the required groups remain active and take part in the reaction under the chosen reaction conditions. Thus, for example, substituents present on any of the reactants used to prepare the compounds according to the invention may be protected. Similarly the $-NR_2^2$ group may be protected during the reaction and deprotected thereafter. Such protection/deprotection procedures are well known in the art, see for example McOmie in "Protective Groups in Organic Chemistry", Plenum, 1973 and T. W. Greene in "Protective Groups in Organic Chemistry", Wiley-Interscience, 1981.

In a further aspect, the present invention thus provides a process for preparing the compounds of the invention comprising the step of derivatising the carboxylic acid group of a 5-aminolevulinic acid or a protected derivative thereof.

The invention can thus be seen to provide a process for preparing the compounds of the invention, said process comprising at least one of the following steps:

(a) reacting a compound of formula II:

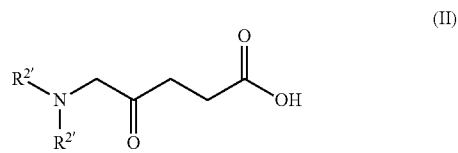

wherein each $R^{2'}$, which may be the same or different, is a group $R^2$ as herein defined or a protected derivative thereof with a compound of formula III:

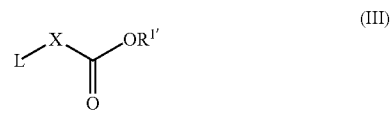

wherein X is as herein defined;
L represents a leaving group, for example a halogen atom; and $R^1$ is a group $R^1$ as herein defined or a protected derivative thereof;

(b) deprotecting a protected derivative of a compound of formula I; and (c) converting a compound of formula I into a pharmaceutically acceptable salt thereof.

The reaction of step (a) may conveniently be carried out in a solvent or mixture of solvents such as water, acetone, ethylacetate, diethylether, methylformamide, tetrahydrofuran, etc., at temperatures up to the boiling point of the mixture, preferably at ambient temperatures. The precise conditions of the reaction will depend on the reactants used and the conditions may be chosen such that maximum yield of the final product is obtained.

The reaction of step (a) will conveniently be carried out in the presence of a catalyst, e.g. an inorganic or organic acid or an acid binding agent such as a base.

The compounds used as starting materials are known from the literature, and in many cases commercially available, or may be obtained using methods known per se. 5-ALA, for example, is available from Sigma-Aldrich or Biosynth AG, Switzerland.

The compounds of the invention preferably take the form of pharmaceutically acceptable and/or skin compatible salts. Such salts preferably are the acid addition salts with physiologically acceptable organic or inorganic acids which have been mentioned hereinbefore.

The compounds of the invention are precursors of photosensitisers, i.e. they can be taken up into cells and converted to protoporphyrins, which are photosensitisers. Hence the compounds of the invention have valuable pharmacological properties, namely as precursors of photosensitisers which renders these useful in methods of photodynamic treatment and photodynamic diagnosis, and in photodynamic cosmetic methods.

Accordingly, a further aspect of the invention provides a composition comprising a compound of formula I as herein described, or a pharmaceutically acceptable salt thereof, together with at least one pharmaceutically acceptable or cosmetically acceptable carrier or excipient.

In a preferred embodiment, the invention provides a pharmaceutical composition comprising a compound of formula I as herein described, or a pharmaceutically acceptable salt thereof, together with at least one pharmaceutically acceptable carrier or excipient.

In another preferred embodiment, the invention provides a cosmetic composition comprising a compound of formula I as herein described, or a pharmaceutically acceptable salt thereof, together with at least one cosmetically acceptable carrier or excipient.

In a further aspect the invention provides a compound or pharmaceutical composition as herein described for use as a medicament, for example in a method of photodynamic treatment or photodynamic diagnosis and especially for the treatment or diagnosis of disorders or abnormalities of external or internal surfaces of the body which are responsive to photodynamic treatment or diagnosis.

In a still further aspect the invention provides the use of a compound of formula I as herein described, or a pharmaceutically acceptable salt thereof, for use in the preparation of a pharmaceutical composition for use in a method of photodynamic treatment or for use in the preparation of a pharmaceutical composition for use in a method of photodynamic diagnosis, and especially for the treatment or diagnosis of disorders or abnormalities of external or internal surfaces of the body which are responsive to photodynamic treatment or diagnosis.

The use of the compounds and pharmaceutical compositions herein described in the photodynamic treatment or diagnosis of cancer, an infection associated with cancer such as a viral infection (e.g. human papilloma virus, hepatitis B or Epstein Barr virus), or bacterial infections (e.g. *Helicobacter pylori* infection), or in the treatment or diagnosis of a non-cancerous condition form preferred aspects of the invention.

As used herein, the terms "cancer" and "cancerous" are used in connection with conditions where malignant cells are present. Pre-malignant conditions are thus not encompassed by these terms.

The term "non-cancerous" includes benign and pre-malignant conditions.

As used herein the term "treatment" or "therapy" encompasses curative as well as prophylactic treatment or therapy.

The abnormalities and disorders which may be treated or diagnosed according to the present invention include any malignant, pre-malignant and benign abnormalities or disorders responsive to photodynamic treatment or diagnosis.

In general, cells which are metabolically active are responsive to photodynamic treatment or diagnosis with the compounds of the invention. Examples of metabolically active cells are cells which undergo an abnormal growth pattern. Such abnormal growth patterns include an increased number of cells/increased cell proliferation (hyperplasia), abnormal maturation and differentiation of cells (dysplasia) and abnormal proliferation of cells (neoplasia). The cells of a hyperplastic growth remain subject to normal regulatory control mechanisms. Cells of a neoplastic growth are genetically abnormal cells which proliferate in a non-physiological manner which is unresponsive to normal stimuli. Other examples of metabolically active cells are inflamed cells.

The compounds and pharmaceutical compositions according to the invention are particularly suited for use in the photodynamic treatment and diagnosis of neoplasms and tumors (benign, pre-malignant and malignant) on internal body surfaces and external body surfaces (e.g. the skin). Examples of such neoplasms and tumors on external body surfaces are actinic keratosis and Bowen's disease. Examples of such neoplasms and tumors on internal body surfaces are bladder cancer and colon cancer.

Further, the compounds and pharmaceutical compositions according to the invention are particularly suited for use in the photodynamic treatment and diagnosis of diseases and disorders associated with viral, bacterial and fungal infections such as acne (associated with the bacterium *Propionibacterium acnes*), vaginal or cervical intraepithelial neoplasia (associated with the human papilloma virus), stomach cancer (associated with the bacterium *Helicobacter pylori*) and pseudomembranous colitis (associated with the bacterium *Clostridium difficile*).

Further, the compounds and pharmaceutical compositions according to the invention are particularly suited for use in the photodynamic treatment of infections of skin or wounds with Gram-positive bacteria. Such infections are often caused by *Staphylococcus aureus* (*S. aureus*), and are commonly treated with antibiotics, e.g. penicillin. There is an unmet medical need to find alternative treatments since many *S. aureus* strains have developed antibiotic resistance. Other Gram-positive bacteria which are involved in bacterial wound infections are for instance *Staphylococcus epidermis, Bacillus subtilis, Enterococcus faecalis*, and *Micrococcus luteus*.

In addition, the compounds and pharmaceutical compositions according to the invention are particularly suited for use in the photodynamic treatment and diagnosis of inflamed cells. Inflammation of cells is usually a protective attempt by the organism to remove injurious stimuli and to initiate the healing process and is thus often associated with an infection. Examples are inflammatory acne, colitis (e.g. inflammatory bowel disease, ulcerative colitis and Crohn's disease), and infective dermatitis, i.e. inflammation of the skin caused by bacterial, viral or fungal infection.

The internal and external body surfaces which may be treated according to the invention include the skin and all other epithelial and serosal surfaces, including for example mucosa, the linings of organs e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumors such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vulva, vagina, uterine cervix, and uterus; (vi) the parietal and visceral pleura; (vii) the lining of the peritoneal and pelvic cavities, and the surface of the organs contained within those cavities; and (viii) the dura mater and meninges.

To obtain the pharmaceutical compositions according to the invention, the compounds according to formula I may be formulated in any conventional manner with one or more physiologically acceptable carriers or excipients, according to techniques well known in the art. Where appropriate, the compounds or compositions according to the invention are sterilized, e.g. by γ-irradiation, autoclaving or heat sterilization, before or after the addition of a carrier or excipient where that is present, to provide sterile formulations.

Pharmaceutical compositions may be administered systemically (e.g. orally or parenterally) or locally (e.g. by injection or topically) at or near the affected site. Topical pharmaceutical compositions are preferred, and include gels, creams, ointments, sprays, lotions, salves, sticks, powders, pessaries, suppositories, aerosols, drops, solutions and any of the other conventional pharmaceutical forms in the art. Topical administration to inaccessible sites may be achieved by techniques known in the art, e.g. by use of catheters or other appropriate drug delivery systems.

Ointments, gels and creams may, for example, be formulated with an aqueous or oily base with the addition of suitable thickening and/or gelling agents. Any thickening or gelling agents used should be non-toxic, non-irritant and devoid of leachable impurities. They should be inert towards the active ingredients, i.e. should not promote its degradation. Formulations for wound treatment, e.g. treatment of bacterial infected wounds, may be based on gel formulations, e.g. hydrogels. The compounds of the invention may be incorporated into such hydrogel formulations. Alternatively, the compounds may be incorporated into liposomes which are incorporated into the hydrogels (see for instance J. Hurler et al., J. Pharm. Sci. 101, No. 10, 2012, 3906-3915). Lotions may be formulated with an aqueous or oily base and will, in general, also contain one or more emulsifying, dispersing, suspending, thickening or colouring agents. Powders may be formed with the aid of any suitable powder base. Drops, sprays and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the pharmaceutical compositions may be provided in a form adapted for oral or parenteral administration, for example by intradermal, subcutaneous, intraperitoneal or intravenous injection. Alternative pharmaceutical forms thus include plain or coated tablets, capsules, suspensions and solutions containing as carriers or excipients corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof. If the pharmaceutical composition according to the invention optionally comprises one or more pharmaceutically acceptable solvents, such solvents may be a free fatty acid, a free fatty alcohol, an aqueous solution, e.g. a buffer, or water.

The pharmaceutical compositions may additionally include common pharmaceutical excipients such as lubricating agents, thickening agents, wetting agents, emulsifying agents, suspending agents, preserving agents, fillers, binders, preservatives, adsorption enhancers, e.g. surface penetrating agents as mentioned below, and the like. Solubilizing and/or stabilizing agents may also be used, e.g. cyclodextrins (CD) α, β, γ and HP-β cyclodextrin. The skilled man will be able to select suitable excipients based on their purpose. Common excipients that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

All of the above-mentioned pharmaceutically acceptable excipients are well known in the art and are commercially available from various manufacturers.

The pharmaceutical compositions of the invention may be formulated so as to provide quick, sustained or delayed release of the active ingredient after administration to the patient by employing procedures well known in the art.

The concentration of the compounds herein described in the pharmaceutical compositions depends upon the nature of the compound, the composition, the mode of administration, the condition to be treated or diagnosed, and the subject to which it is administered and may be varied or adjusted according to choice. Generally, however, concentration ranges of 0.01 to 50% by weight, such as 0.05 to 20% by weight, or 1 to 10% by weight, e.g. 1 to 5% by weight, are suitable. It will be appreciated that PDT may require higher concentrations of the compounds of the invention than used in the diagnostic methods.

In another embodiment, the pharmaceutical compositions may further comprise one or more bioadhesive agents, e.g. mucoadhesive agents as described in WO 02/09690 to Photocure ASA, the entire contents of which are incorporated herein by reference.

The compounds of the invention may be formulated and/or administered with other active components which serve to enhance the photodynamic effect, for example surface penetration assisting agents (or penetration enhancers) and/or chelating agents. Suitable surface penetration assisting agents and chelating agents and suitable concentrations of such agents are described in WO 2009/074811 to Photocure ASA, the entire contents of which are incorporated herein by reference. Dependent on the nature of the composition, the compounds may be co-administered with such other optional agents, for example in a single composition or, alternatively, they may be administered separately (e.g. sequentially). In some cases it may be beneficial to pre-treat the external or internal surface of the body to be treated with a surface penetration assisting agent in a separate step prior to administration of the active component. When a surface penetration assisting agent is used in a pre-treatment step, this may be used at higher concentrations, e.g. up to 100% by weight. If such a pre-treatment step is used, the pharmaceutical composition according to the invention may subsequently be administered up to several hours following pre-treatment, e.g. at an interval of 5 to 60 minutes following pre-treatment.

Products and kits which comprise a pharmaceutical composition as herein described and, optionally, a surface penetration assisting agent and/or a chelating agent, as a combined preparation for simultaneous, separate or sequential use in a method of photodynamic treatment or diagnosis of an abnormality of an external or internal surface of the body form a further aspect of the invention.

Alternatively viewed, this aspect of the invention provides a kit for use in a method of photodynamic treatment or diagnosis of a disease, disorder or abnormality of an external or internal surface of the body, said kit comprising:
 (a) a first container containing a compound as herein described, or a pharmaceutically acceptable salt thereof, or a pharmaceutical composition as herein described;
 (b) a second container containing at least one surface penetration assisting agent; and optionally
 (c) one or more chelating agents contained either within said first container or in an optional third container.

A further aspect of the invention provides a method of photodynamic treatment or diagnosis of a disease, disorder or abnormality of an external or internal surface of the body, said method comprising administering to the affected surface a pharmaceutical composition as herein described and exposing said surface to light.

After administration of the pharmaceutical composition to the external or internal surface of the body, the desired area for treatment or for examination (in the case of diagnosis) is exposed to light (irradiation) to achieve the desired photoactivation. The length of time period between administration and exposure to light, i.e. the incubation time, will depend on the nature of the compound, the nature of the composition, the condition to the treated or diagnosed, and the mode of administration. Generally, it is necessary that the compound of the invention within the pharmaceutical composition is sufficiently released to be taken up by the cells of the tissue to be treated or diagnosed, converted into a photosensitiser and achieves an effective tissue concentration at the intended treatment/diagnosis site prior to photoactivation. Typically, the incubation time will be up to 10 hours, for example about 10 minutes to 10 hours, e.g. 30 minutes to 7 hours, or 1 hour to 5 hours. Direct local administration may result in shorter incubation times, for example, no incubation time at all (i.e. intermediate exposure to light after administration), about 1 minute to 3 hours, e.g. 5 minutes to about 2 hours, or 15 minutes to 1.5 hours or 30 minutes to 1 hour. Where systemic uptake is required following oral administration, the incubation time may be longer, for example between about 30 minutes and 6 hours, e.g. 2 to 5 hours or 3 to 4 hours. Optimum incubation times to maximise the concentration of the photosensitiser at the target site may readily be determined, e.g. by fluorescence measurements over time.

The irradiation will generally be applied for a short time with a high light intensity, i.e. a high fluence rate, or for a longer time with a low light intensity, i.e. low fluence rate. The latter may be preferred for a PDT procedure, especially when the patient is not anaesthetized. Low light intensity PDT procedures result in reduced discomfort to the patient without any reduction in efficacy of the treatment. However, if the PDT or PDD procedure requires anesthesia and/or immobilisation of the patient and/or needs to be carried out in an operating theatre, irradiation applied for a short time with a high light intensity, i.e. a high fluence rate may be preferred. The fluence rate is dependent on the means of irradiation, i.e. on the particular lamp or laser used. The fluence rate may be an immanent parameter which cannot be chosen by the user of the lamp/laser. However, if the fluence rate can be chosen, for lamps comprising light emitting diodes, generally fluence rates of 0.5 to 100 mW/cm$^2$ may be chosen. For a low fluence rate procedure, fluence rates below 50 mW/cm$^2$ are preferred. More preferred are fluence rates in the range 1-30 mW/cm$^2$, most preferably in the range 2 to 10 mW/cm$^2$. For a high fluence rate procedure, fluence rates above 50 mW/cm$^2$ are preferred, more preferably in the range 50 to 70 mW/cm$^2$.

The wavelength of the light used for irradiation may be selected to achieve the desired photodynamic effect. Irradiation with wavelengths of light in the range 300-800 nm, e.g. 400-700 nm and 500-700 nm, has been found to be particularly effective. For PDT, it can be particularly important to include the wavelengths 630 and 690 nm. Red light (600 to 670 nm) is particularly preferred since light at this wavelength is known to penetrate well into tissue. For PDD, the area of interest may first be examined using white light. For the actual photodynamic diagnosis, blue light having a wavelength typically ranging from 360 to 450 nm will generally be used, giving rise to fluorescence in the red region (e.g. 550 to 750 nm) which can be visually detected or measured by suitable spectrometers.

The irradiation for PDT will in general be applied at a light dose of from 10 to 200 J/cm$^2$, preferably from 20 to 100 J/cm$^2$ and most preferably from 25 to 60 J/cm$^2$. For PDD, irradiation is preferably performed during the whole diagnostic procedure or during a part thereof, e.g. when combined with white light detection. For both PDT and PDD, a single irradiation may be used or alternatively a light split dose in which the light dose is delivered in a number of fractions, e.g. a few minutes to a few hours between irradiations, may be used. Multiple irradiations may also be applied.

The duration of irradiation for PDT (i.e. irradiation time) is dependent on the fluence rate of the irradiation device and the desired light dose. Essentially, the light dose is the product of irradiation time and fluence rate.

Various irradiation means are known in the art, e.g. laser and lamps. The latter may be lamps comprising a light bulb, e.g. a short arc xenon bulb or a fluorescent tube. Alternatively, the lamp may comprise light emitting diodes or organic light emitting diodes (LEDs and OLEDs). For irradiation of internal surfaces of the body, e.g. the lining of the bladder or the colon, endoscopes may be used. Usually, endoscopes comprise an external light source (e.g. laser or lamp) which is coupled to an optical fibre which functions as a waveguide to transmit the light from the external light source to the area of interest.

In a further aspect the invention thus provides a method of in vivo imaging of a target site at an internal or external surface of the body, said method comprising the following steps:
 (a) administering to a subject, e.g. a human or non-human animal, a compound as herein described, a pharmaceutically acceptable salt thereof, or a pharmaceutical composition comprising said compound or said salt;
 (b) if necessary, waiting for a time period necessary for the compound or pharmaceutically acceptable salt thereof to be taken up by the cells of said target site, converted into a photosensitiser and achieve an effective concentration at the target site;
 (c) exposing the target site to light whereby to photoactivate the photosensitiser;
 (d) detecting a fluorescence indicative of an abnormality of the target site; and
 (e) optionally converting the detected fluorescence into an image of an area of interest.

In a preferred embodiment of this aspect of the invention, the method of imaging may be performed on a subject pre-administered with said compound, a pharmaceutically acceptable salt thereof, or a pharmaceutical composition comprising said compound or said salt.

The PDD procedures described herein may also be performed during surgery in which a compound of the invention or a pharmaceutical composition comprising said compound is administered to the patient and surgery is then performed under blue light. The fact that the abnormalities fluoresce under blue light aids the surgeon in defining the "surgical border" and thereby enables a more selective resection of the diseased area (e.g. tumor). Use of the compounds and pharmaceutical compositions herein described in methods of surgery forms a further aspect of the invention.

The therapeutic and diagnostic methods herein described may also be used in the form of a combined therapy. For example, a course of PDT performed in relation to an abnormality, disorder or disease of an internal or external surface of the body using a compound or composition as herein described may be followed by a PDD method (e.g. to determine the extent to which PDT has been effective and/or to detect any re-occurrence of the condition).

In a further aspect the invention thus provides a compound or composition as herein described for use in a method which comprises the steps of: (i) conducting photodynamic treatment of an abnormality, disorder or disease of an internal or external surface of the body of a patient; and (ii) conducting photodynamic diagnosis on said patient. At least one of steps (i) and (ii) is performed following administration to said patient of a compound or pharmaceutical composition according to the invention. Preferably, steps (i) and (ii) will both be performed following administration of such a compound or composition.

Following identification of an abnormality, disorder or disease of an internal or external surface of the body using any of the methods herein described, this may then be treated through alternative therapeutic techniques, e.g. by surgical or chemical treatment. Examples of current treatments include surgical treatment, endoscopic ablation therapy, chemical ablation, thermal ablation or mechanical ablation. In one embodiment of the invention, further application of the compound or pharmaceutical composition at the site of interest may be carried out in order to effect PDT.

The compounds of the invention may also be used for in vitro diagnostic techniques, for example examination of the cells contained in body fluids. The higher fluorescence associated with metabolically active cells may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, spinal fluid etc. Tissue samples or preparations may also be evaluated, for example biopsy tissue or bone marrow samples. The present invention thus extends to the use of compounds of the invention, or pharmaceutically acceptable salts thereof for photodynamic diagnosis, and products and kits for performing said diagnosis.

A further aspect of the invention relates to a method of in vitro diagnosis of abnormalities, disorders or diseases of an internal or external surface of the body of a patient by assaying a sample of body fluid or tissue of said patient, said method comprising at least the following steps:
i) admixing said sample of body fluid or tissue with a compound as described hereinbefore, a pharmaceutically acceptable salt thereof or a pharmaceutical composition comprising said compound or said salt,
ii) exposing said mixture to light,
iii) ascertaining the level of fluorescence, and
iv) optionally comparing the level of fluorescence to control levels.

The compounds according to the invention may also be used in the photodynamic treatment of abnormalities, disorders or diseases of an internal or external surface of the body caused by or otherwise associated with bacteria, including pathogenic bacteria or conditionally pathogenic bacteria, i.e. bacteria that are part of the normal human flora but may be pathogenic under certain conditions.

Multi-drug resistance is an increasing problem in the field of infectious diseases. Amongst the many species of pathogenic bacteria which have become resistant to conventional antibiotics is *Staphylococcus aureus* (*S. aureus*) which is responsible for causing skin infections as well as infecting wounds and burns. Toxic strains of *S. aureus* can enter the bloodstream as a result of such infections and this in turn may lead to serious complications and even life-threatening conditions such as toxaemia (toxic shock syndrome), endocarditis and pneumonia. Resistant strains of *S. aureus* include methicillin-resistant *S. aureus* (MRSA).

The compounds herein described, when used in PDT, have been found to be effective in killing, or at least reducing the proliferative potential of bacterial cells, in particular Gram-positive bacteria, especially *Staphylococcus aureus*.

Viewed from a further aspect the invention thus provides a compound or pharmaceutical composition as herein described for use in a method of treatment and/or prevention of a bacterial infection, e.g. for use in a method of treatment or prevention of a condition caused by or associated with drug-resistant bacteria. Methods of medical treatment of such conditions in which an effective amount of the compound or composition is administered to a patient in need thereof form a further aspect of the invention.

In infants, *S. aureus* infection can cause a severe disease—staphylococcal scalded skin syndrome (SSSS). The disease presents with the widespread formation of fluid filled blisters that are thin walled and easily ruptured. Further, *S. aureus* is extremely prevalent in atopic dermatitis patients who are less resistant to it than other people. It often causes complications, and this disease is mostly found in fertile, active places, including the armpits, hair, and scalp.

As previously described, the compounds according to the invention also find particular use in photodynamic cosmetic methods. Accordingly, in a further aspect the invention provides a cosmetic composition comprising a compound of formula I or a pharmaceutically acceptable salt thereof, together with at least one skin compatible carrier or excipient.

The term "cosmetic" as used herein in relation to any composition, product, kit, method or use is intended to define a product or treatment method which is used or intended for use for cosmetic purposes, i.e. to enhance, improve or maintain the general cutaneous appearance of the individual to whom it is administered.

The term "skin compatible" denotes a substance that is suitable for use in a cosmetic dermal composition, e.g. in a composition for use on the skin of mammals, especially humans. A "skin compatible" carrier or excipient is usually non-irritant and well-tolerated.

To obtain the cosmetic compositions according to the invention, the compounds of formula I may be formulated in any conventional manner with one or more skin compatible carriers or excipients, according to techniques well known in the art. Where appropriate, the compounds of compositions may be sterilized using methods as hereinbefore described in relation to the pharmaceutical compositions.

Cosmetic compositions are topically administered to the skin. Suitable cosmetic compositions include gels, creams, ointments, sprays, lotions, salves, sticks, powders, solutions and any of the other conventional cosmetic formulations of the art.

Cosmetic ointments, gels, lotions, salves and creams may, for example, be formulated with an aqueous or oily base (preferred for ointments and salves) with the addition of suitable thickening and/or gelling agents. Any thickening or gelling agents used should be non-toxic, non-irritant and devoid of leachable impurities. They should be inert towards the compounds of the invention, i.e. should not promote their degradation. Lotions and creams may be formulated with an aqueous or oily base and will, in general, also contain one or more emulsifying, dispersing, suspending, thickening or colouring agents. Powders may be formed with the aid of any suitable powder base. Sprays and solutions may be formulated with an aqueous or non-aqueous base also comprising one or more dispersing, solubilising or suspending agents.

The cosmetic compositions may additionally include common cosmetic excipients such as lubricating agents, thickening agents, wetting agents, emulsifying agents, suspending agents, preserving agents, perfumes, fillers, binders and preservatives. They may further comprise surface penetrating agents as mentioned below, and the like. The skilled man will be able to select suitable excipients based on their purpose. Common excipients that may be used in the cosmetic products herein described are listed in various handbooks (e.g. E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)). Further, suitable skin compatible excipients and carriers and suitable amounts thereof for use in the cosmetic compositions according to the invention are disclosed in WO 2011/107478 to Photocure ASA, the entire contents of which are incorporated herein by reference.

All of the above-mentioned cosmetic excipients are well known in the art and are commercially available from various manufacturers.

The desired amount of the compounds of the invention in the cosmetic compositions will be dependent on several factors, including the specific nature of the formulation, whether or not a light source is used in the cosmetic treatment and if so, the type of light source and the selected wavelength, the duration of the cosmetic treatment and the overall number of treatments. Taking into account these various factors, the amount may readily be determined by those skilled in the art. The cosmetic composition according to the invention will generally comprise 5% by weight or less of the compounds of the invention, preferably 0.02 to 3% by weight, more preferably 0.05 to 1.5% by weight, e.g. 0.5 to 1.25% by weight and most preferably 0.1 to 1.0% by weight, with the range of 0.25 to 0.75% by weight being the most preferred one. In determining the desired amount within these ranges, the following criteria within the knowledge and expertise of those skilled in the art may also be considered:

cosmetic compositions which are capable of penetrating more deeply into the skin, e.g. due to the nature of the composition, the nature of the selected compound of the invention or due to the presence of agents which promote deeper penetration, e.g. skin penetration enhancing agents, will typically contain a lower concentration of the compounds of the invention than compositions which tend to remain primarily on the surface of the skin;

cosmetic compositions intended for longer durations of skin treatment (i.e. longer incubation of the composition on the skin and/or longer illumination) normally contain less of the compounds of the invention than compositions intended for shorter durations of treatment;

cosmetic compositions intended for more than one course of skin treatment, e.g. several or many treatments such as several treatments over a period or repeated treatments, normally contain less of the compounds of the invention than compositions intended for use once or intended for use a limited number of times, often with a delay between each treatment;

cosmetic compositions intended for the treatment of skin with only few signs of (photo)aging may contain less of the compounds of the invention than compositions intended for treatment of severely (photo)aged skin.

The cosmetic compositions according to the invention may be used in a method of cosmetic treatment. Such a cosmetic treatment can be carried out for enhancing and/or improving the appearance of the skin of a mammalian subject, preferably a human subject. In particular, signs of (photo)aging may be improved, e.g. reducing the appearance of crow's feet, dark circles, fine lines, wrinkles, decreasing pore size and improving skin firmness and elasticity.

Suitable light sources for such cosmetic treatments as well as suitable fluence rates, irradiation times, light doses and wavelengths are disclosed in detail in WO 2011/107478 to Photocure ASA, the entire contents of which are incorporated herein by reference.

The invention is illustrated by the following non-limiting examples and with reference to the accompanying figures in which:

FIG. 1 shows the fluorescence from minipig skin after application of a cream formulation of carboxymethyl 5-amino-4-oxopentanoate hydrobromide.

Figure 2:
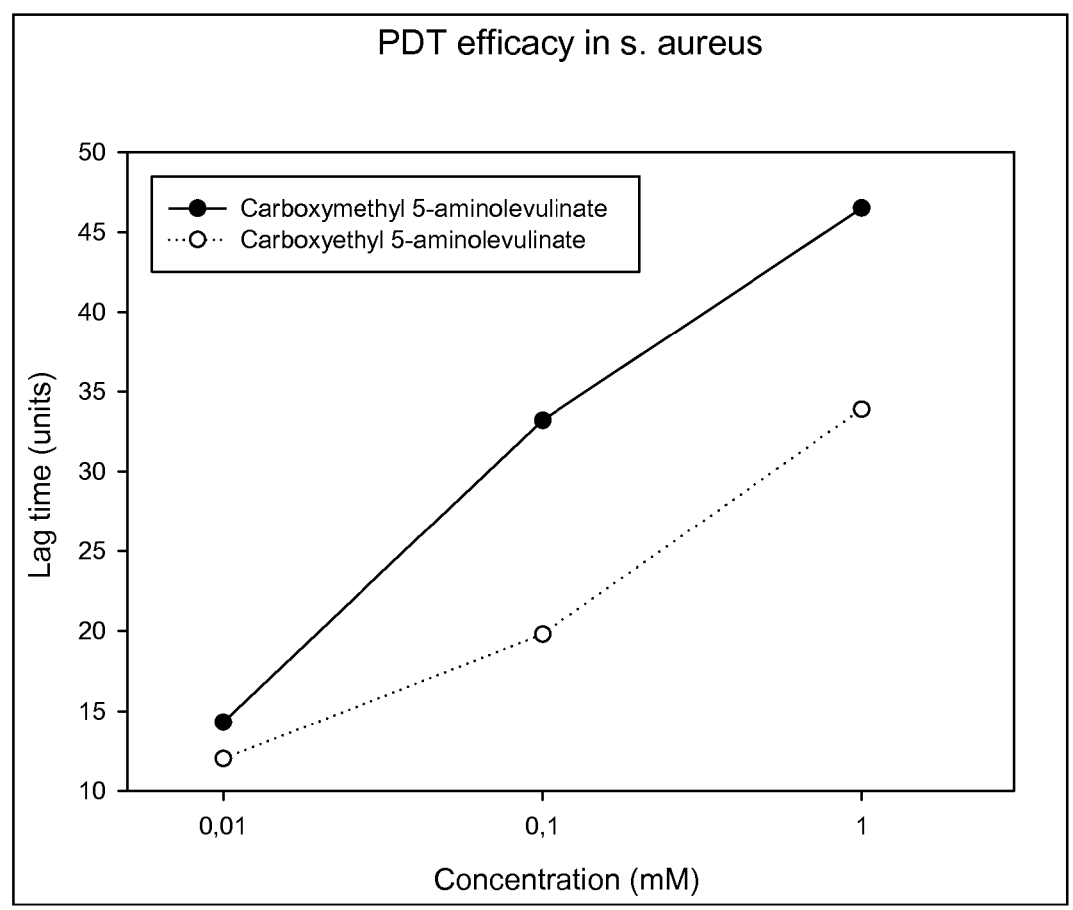

FIG. 2 shows the delay in growth of *S. aureus* bacteria incubated with carboxymethyl 5-amino-4-oxopentanoate hydrobromide and 2-carboxyethyl 5-amino-4-oxopentanoate hydrobromide due to photodynamic effects.

The following abbreviations are used in the Examples:
Boc—tert-butoxycarbonyl
Cbz—carboxybenzyl
dec—decomposes

EXAMPLE 1

Preparation of Carboxymethyl
5-Amino-4-Oxopentanoate Hydrohalides
(Hydrochloride and Hydrobromide)

1a—Preparation of t-butoxycarbonylmethyl
5-(Boc-amino)-4-oxopentanoate

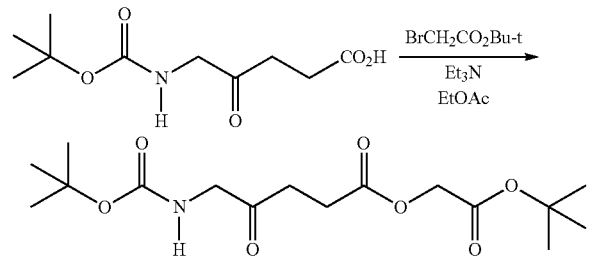

Triethylamine (2.22 g; 22.0 mmol) was added dropwise to a stirred solution of 5-(Boc-amino)-4-oxopentanoic acid (4.62 g; 20.0 mmol) and t-butyl bromoacetate (4.30 g; 22.0 mmol) in ethyl acetate (60 mL) under argon at ambient temperature. The mixture (slurry) was refluxed for 17 h, then cooled to ambient temperature, poured into 0.5 M HCl (100 mL) and shaken thoroughly. The aqueous portion was extracted with ethyl acetate (2×20 mL). The combined organic solutions were washed with saturated NaHCO$_3$ solution (1×20 mL) and saturated NaCl solution (1×20 mL) then dried (MgSO$_4$), filtered and evaporated. Evaporation resulted in an amber oil that was purified by flash chromatography on a 40×55-mm silica gel 60 column eluted with ethyl acetate-hexane (1:1) (600 mL), collecting 5×100 mL fractions. Evaporation of fractions 1 and 2 resulted in 6.15 g (89%) product (yellow oil).

$^1$H NMR: (200 MHz; CDCl$_3$): δ 1.44 (9H, s), 1.47 (9H, s), 2.77 (4H, s), 4.06 (2H, d, J=4.8 Hz), 4.49 (2H, s), 5.25 (1H, br s).

$^{13}$C NMR: (50 MHz; CDCl$_3$): δ 27.5, 28.0, 28.3, 34.2, 50.3, 61.3, 79.8, 82.5, 155.5, 166.5, 171.7, 203.9.

1b—Preparation of carboxymethyl 5-amino-4-oxopentanoate hydrochloride

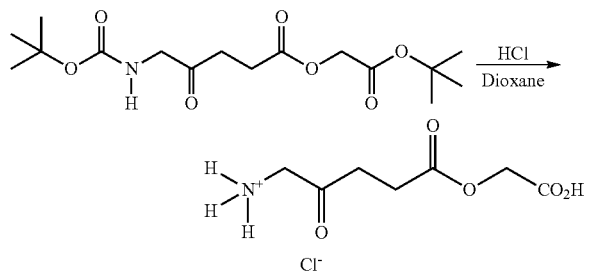

A 4 M solution of hydrogen chloride in dioxane (35 mL; 0.14 mol) was added to the product of 1a (3.3 g; 9.5 mmol) and stirred until the oil dissolved with evolution of gas. After standing one hour, the solvent was evaporated and the residue was triturated with diethyl ether (4×20 mL); the oil solidified to a tan powder. The residue was filtered and dried overnight in a drying pistol at 50° C. and 13 mm Hg. 2.05 g (96%) product was obtained (tan powder).

$^1$H NMR: (300 MHz; DMSO-d$_6$): δ 2.65 (2H, t, J=6.2 Hz), 2.82 (2H, t, J=5.9 Hz), 3.96 (2H, br s), 4.57 (2H, s), 8.40 (3H, br s).

$^{13}$C NMR: (75 MHz; DMSO-d$_6$): δ 26.7, 34.1, 46.5, 60.7, 168.8, 171.5, 202.3.

1c—Preparation of carboxymethyl 5-amino-4-oxopentanoate hydrobromide

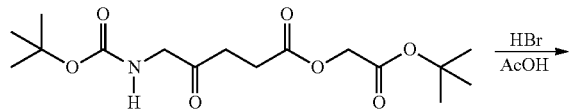

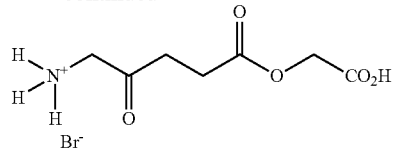

A 30% solution of hydrogen bromide in acetic acid (12 mL) was added to the product of 1a (3.3 g; 9.5 mmol) cooled with an ice-water bath and stirred until the oil dissolved with evolution of gas. After stirring for 15 min, the mixture was triturated with hexane (4×20 mL) and diethyl ether (4×20 mL); the oil solidified to a tan powder. The residue was filtered and dried overnight in a drying pistol at ~50° C. and 12 mm Hg. 4.44 g (92%) product was obtained (tan powder, mp 110-114° C. (dec.)).

$^1$H NMR: (300 MHz; DMSO-d$_6$): δ 2.66 (2H, t, J=6.6 Hz), 2.85 (2H, t, J=6.6 Hz), 4.02 (2H, d, J=4.8 Hz), 4.57 (2H, s), 8.14 (3H, br s).

$^{13}$C NMR: (75 MHz; DMSO-d$_6$): δ 26.7, 34.1, 46.6, 60.6, 168.8, 171.5, 202.3.

EXAMPLE 2

Preparation of 1-(isopropyl carboxy)ethyl 5-amino-4-oxopentanoate hydrochloride

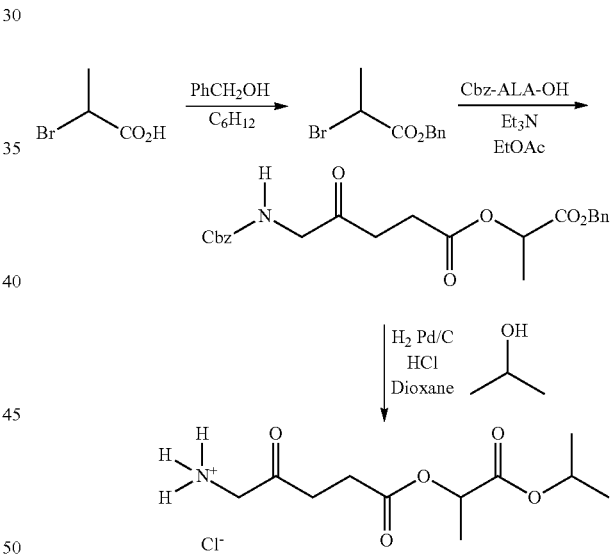

2a—Preparation of benzyl 2-bromopropanoate

A mixture of 2-bromopropanoic acid (15.3 g; 100 mmol), benzyl alcohol (13.0 g; 120 mmol) and p-toluenesulphonic acid monohydrate (50 mg) in cyclohexane (200 mL) was refluxed in a Dean-Stark apparatus for 19 h. The reaction mixture was cooled to ambient temperature, washed with saturated NaHCO$_3$ solution (1×30 mL), water (1×30 mL) and saturated NaCl solution (1×30 mL). After drying (MgSO$_4$), filtration, and evaporation, the residue was vacuum-distilled. 25.4 g (87%) product was obtained (colourless liquid, by 111-113° C./1.1 mm Hg).

$^1$H NMR: (200 MHz; CDCl$_3$): δ 1.83 (3H, d, J=7.0 Hz), 4.40 (1H, q, J=7.0 Hz), 5.20 (2H, s), 7.36 (5H, s).

$^{13}$C NMR: (50 MHz; CDCl$_3$): δ 21.6, 39.9, 67.5, 128.0, 128.4, 128.5, 135.0, 169.9.

2b—Preparation of 1-(benzyloxycarbonyl)ethyl 5-(Cbz-amino)-4-oxopentanoate

Triethylamine was added drop-wise to a stirred solution of 5-(Cbz-amino)-4-oxopentanoic acid (4.00 g; 15.0 mmol) and the product of 2a (3.65 g; 15.0 mmol) in ethyl acetate (50 mL). The stirred mixture was refluxed for 2 days under argon. After cooling to ambient temperature, 0.5 M HCl solution (50 mL) was added and the mixture was shaken thoroughly. The aqueous layer was extracted with ethyl acetate (2×20 mL). The combined ethyl acetate solutions were washed with saturated NaHCO$_3$ solution (2×15 mL) and saturated NaCl solution (1×15 mL), then dried (MgSO$_4$). After filtration and evaporation an amber oil was obtained that was purified by flash chromatography on a 60×55 mm silica gel 60 column eluted with ethyl acetate-hexane (1:1) (1000 mL), collecting 8×100 mL fractions. Evaporation of fractions 3-5 resulted in 4.92 g (77%) product (oil).

$^1$H NMR: (300 MHz; DMSO-d$_6$): δ 1.41 (3H, d, J=7.0 Hz), 2.56 (2H, t, J=6.3 Hz), 2.68 (2H, t, J=6.3 Hz), 4.03 (2H, d, J=7.1 Hz), 5.04 (2H, s), 5.06 (1H, q, J=6.2 Hz), 5.16 (2H, s), 7.36 (10H, m), 7.54 (1H, br s).

$^{13}$C NMR: (75 MHz; DMSO-d$_6$): δ 16.6, 26.9, 33.5, 49.6, 65.4, 66.1, 68.4, 127.6, 127.8, 128.3, 128.4, 135.6, 137.0, 156.3, 170.1, 171.6, 205.2.

2c—Preparation of 1-(isopropyl carboxy)ethyl 5-amino-4-oxopentanoate hydrochloride A stirred mixture of the product of 2b (4.92 g; 11.5 mmol), 10% palladium on activated carbon (100 mg), hydrogen gas and 2.0 M hydrogen chloride in diethyl ether (10 mL; 20 mmol) in 2-propanol (15 mL) and dioxane (15 mL) was hydrogenated at ca. 6 bar for 2 days at ambient temperature. The mixture was filtered through a Celite® 545 pad and the residue was washed with 2-propanol (2×5 mL). The combined filtrates were evaporated and the resulting oil was triturated with diethyl ether (4×10 mL), then stored in a freezer. The oil did not solidify. After vacuum-drying (at 0.005 mm Hg) overnight, 1.97 g (71%) product was obtained (tan, viscous oil).

$^1$H NMR: (300 MHz; DMSO-d$_6$): δ 1.17 (6H, dd, J=5.7 Hz), 1.37 (3H, d, J=7.0 Hz), 2.60 (2H, t, J=6.2 Hz), 2.80 (2H, t, J=6.4 Hz), 3.93 (2H, br s), 4.88 (2H, m), 8.38 (3H, br s).

$^{13}$C NMR: (75 MHz; DMSO-d$_6$): δ 16.6, 21.3, 26.8, 34.1, 46.5, 68.5, 68.7, 169.7, 171.5, 202.3.

EXAMPLE 3

Preparation of carboxydifluoromethyl 5-amino-4-oxopentanoate hydrochloride

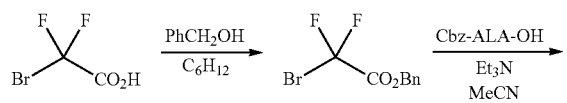

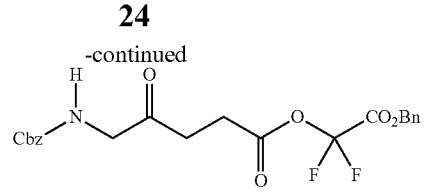

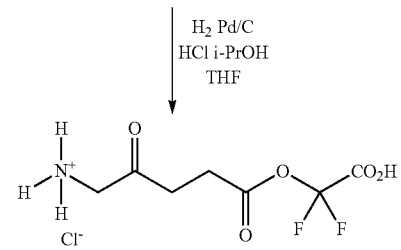

3a—Preparation of benzyl bromodifluoroacetate

This compound was prepared according to Example 2a from bromodifluoroacetic acid (9.82 g; 68.7 mmol), benzyl alcohol (7.0 g; 65 mmol), and p-toluenesulphonic acid monohydrate (50 mg) in cyclohexane (120 mL). The crude product obtained after evaporation was used as is without any further workup in 3b.

$^1$H NMR: (300 MHz; CDCl$_3$): δ 5.35 (2H, s), 7.39 (5H, s).
$^{13}$C NMR: (75 MHz; CDCl$_3$): δ 69.8, 108.8 (t, J$_{C-F}$=312 Hz), 128.6, 128.9, 129.2, 140.8, 159.5 (t, J$_{C-F}$=31 Hz).

3b—Preparation of (benzyloxycarbonyl)difluoromethyl 5-(Cbz-amino)-4-oxopentanoate Triethylamine (3.5 mL; 2.5 g; 25 mmol) was added using a syringe to a stirred mixture of the crude product of 3a (8.6 g; 20 mmol) and 5-(Cbz-amino)-4-oxopentanoic acid (6.63 g; 25 mmol) in dry acetonitrile (100 mL). The mixture was refluxed for 18 h, then the solvent was evaporated and the dark red residue was dissolved in diethyl ether (100 mL) and 0.5 M HCl (100 mL). After mixing thoroughly, the ether layer was washed with water (2×15 mL), saturated NaHCO$_3$ (2×15 mL), and saturated NaCl solution (1×15 mL), then dried (MgSO$_4$). After filtration and evaporation, the residue was purified by flash chromatography on a 60×55 mm silica gel 60 column eluted with dichloromethane-diethyl ether (9:1) (1000 mL), collecting 10×75 mL fractions. After evaporation of fractions 2-5 and vacuum-drying (0.02 mm Hg), 6.7 g (74%) product was obtained (red-orange solid mp 48-50° C.).

$^1$H NMR: (300 MHz; DMSO-d$_6$): δ 2.56 (2H, t, J=6.4 Hz), 2.73 (2H, t, J=6.2 Hz), 3.90 (2H, d, J=5.9 Hz), 5.05 (2H, s), 5.08 (2H, s), 7.36 (10H, s), 7.54 (1H, t, J=5.7 Hz).

$^{13}$C NMR: (75 MHz; DMSO-d$_6$): δ 27.2, 33.7, 49.6, 65.42, 65.44, 101.1, 127.6, 127.7, 127.8, 127.9, 128.27, 128.33, 136.1, 137.0, 156.3, 172.0, 174.8, 205.5.

3c—Preparation of carboxydifluoromethyl 5-amino-4-oxopentanoate hydrochloride This compound was prepared from the product of 3b (4.0 g; 8.9 mmol), 10% palladium on carbon (0.20 g), hydrogen gas, and 2 M HCl in diethyl ether (10 mL; 20 mmol) in 2-propanol (75 mL) and tetrahydrofuran (25 mL) as described in Example 2c. After filtration through Celite®, the solution was refiltered through a fluted paper filter. After evaporation, a pale amber oil was obtained that was triturated with diethyl ether (4×10 mL), resulting in 1.6 g (80%) product (pale tan gummy solid). The obtained product was a mixture that contained mainly carboxydifluoromethyl 5-amino-4-oxopentanoate hydrochloride, some isopropyl 5-amino-4-oxopentanoate hydrochloride as well as some 1-(isopropyl carboxy) difluoromethyl 5-amino-4-oxopentanoate hydrochloride. Carboxydifluoromethyl 5-amino-4-oxopentanoate hydrochloride can be isolated from the mixture by standard methods, e.g. preparative HPLC.

$^1$H NMR: (300 MHz; DMSO-$d_6$): δ 2.63 (2H, t, J=6.3 Hz), 2.83 (2H, t, J=6.5 Hz), 3.96 (2H, br s), 8.37 (3H, br, s).

$^{13}$C NMR: (75 MHz; DMSO-$d_6$): δ 27.3, 34.2, 46.5, 171.4, 171.8, 202.5.

EXAMPLE 4

Preparation of 2-carboxyethyl 5-amino-4-oxopentanoate hydrobromide

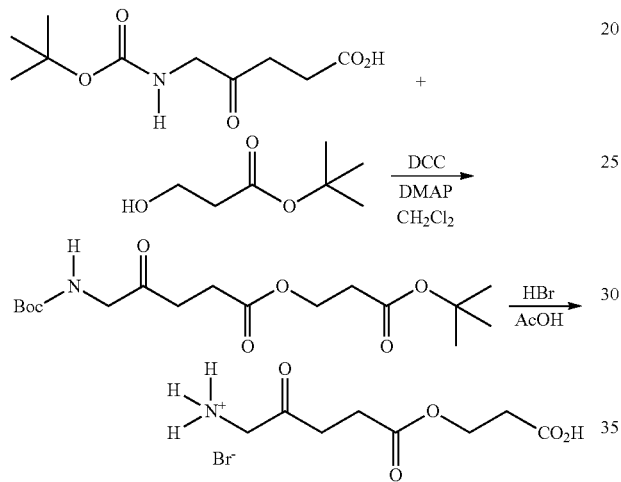

4a—Preparation of 2-(t-butoxycarbonyl)ethyl 5-(Boc-amino)-4-oxopentanoate

A solution of N,N'-dicyclohexylcarbodiimide (DCC, 3.34 g; 16.2 mmol) in dry dichloromethane (20 mL) was added using a syringe to a stirred mixture of 5-(Boc-amino)-4-oxopentanoic acid (3.70 g; 16.0 mmol), t-butyl 3-hydroxypropanoate (2.31 g; 15.8 mmol), and 4-dimethylaminopyridine (DMAP, 50 mg) in dichloromethane (40 mL) at ambient temperature under argon. The mild exothermic reaction was moderated with an ice-water bath. After stirring 2 days at ambient temperature, the mixture was suction-filtered on a glass-sinter filter. The residue was washed with dichloromethane (3×20 mL). The combined filtrates were evaporated and the residue was purified by flash chromatography on a 45×55 mm silica gel 60 column eluted with ethyl acetate-hexane (1:1) (500 mL), collecting 7×50 ml fractions. After evaporation of fractions 2-4, 5.45 g (96%) product was obtained (pale yellow oil).

$^1$H NMR: (300 MHz; DMSO-$d_6$): δ 1.38 (9H, s), 1.41 (9H, s), 2.49 (2H, t, J=6.6 Hz), 2.53 (2H, t, J=6.2 Hz), 2.66 (2H, t, J=6.4 Hz), 3.76 (2H, d, J=5.9 Hz), 4.16 (2H, t, J=6.2 Hz), 7.06 (1H, t, J=5.8 Hz).

$^{13}$C NMR: (75 MHz; DMSO-$d_6$): δ 27.1, 27.6, 28.1, 33.5, 34.3, 49.4, 59.9, 78.0, 80.1, 155.7, 169.6, 171.9, 205.8.

4b—Preparation of 2-carboxyethyl 5-amino-4-oxopentanoate hydrobromide

This compound was prepared from the product of 4a (5.43 g; 15.1 mmol) and 30% HBr in acetic acid (15 mL) according to Example 1c. 3.38 g (79%) product was obtained (amber gum that did not solidify).

$^1$H NMR: (300 MHz; DMSO-$d_6$): δ 2.55 (4H, t, J=6.4 Hz), 2.80 (2H, t, J=6.3 Hz), 4.00 (2H, d, J=3.5 Hz), 4.19 (2H, t, J=6.3 Hz), 8.10 (3H, br s).

$^{13}$C NMR: (75 MHz; DMSO-$d_6$): δ 26.9, 33.2, 34.1, 46.6, 60.1, 171.8 (2C), 202.6.

EXAMPLE 5

Preparation of 3-carboxypropyl 5-amino-4-oxopentanoate hydrochloride

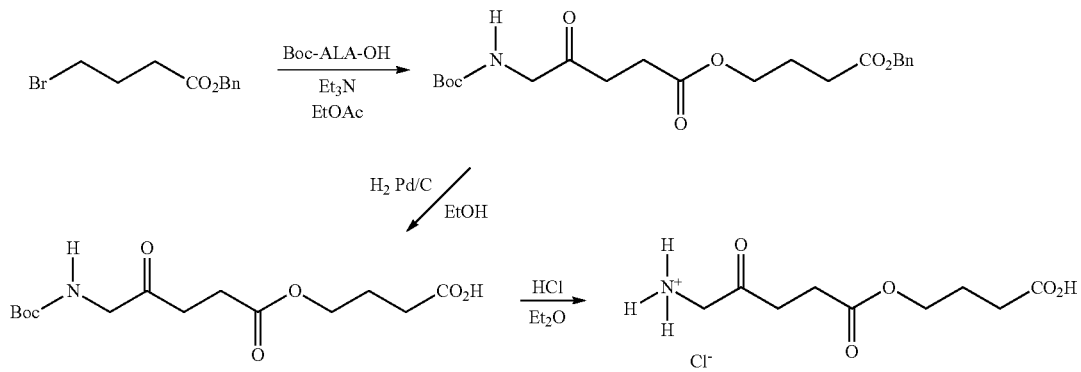

5a—Preparation of 3-(benzyloxycarbonyl)propyl 5-(Boc-amino)-4-oxopentanoate

This compound was prepared from benzyl 4-bromobutanoate (7.2 g; 28.0 mmol), 5-(Boc-amino)-4-oxopentanoate (6.7 g; 29.0 mmol), triethylamine (2.95 mmol), and ethyl acetate (100 mL) as described in Example 1a. The crude product was purified by flash chromatography on a 60×55 mm silica gel 60 column eluted with ethyl acetate-hexane (1:2) (750 mL) collecting 6×100 mL fractions. After evaporation of fractions 3 and 4, 5.43 g (46%) product was obtained (yellow oil).

$^1$H NMR: (300 MHz; DMSO-d$_6$): δ 1.38 (9H, s), 1.85 (2H, m), 2.41-2.50 (4H, m), 2.67 (2H, t, J=6.7 Hz), 3.77 (2H, d, J=5.8 Hz), 4.02 (2H, t, J=6.4 Hz), 5.10 (2H, s), 7.07 (1H, t, J=5.7 Hz), 7.37 (5H, s).
$^{13}$C NMR: (75 MHz; DMSO-d$_6$): δ 23.6, 27.2, 28.1, 30.0, 33.6, 49.4, 63.0, 65.4, 78.0, 127.87, 127.93, 128.4, 136.1, 155.7, 172.1, 172.2, 206.0.

5b—Preparation of 3-carboxypropyl 5-(Boc-amino)-4-oxopentanoate

This compound was prepared from the product of 5a (5.40 g; 13.2 mmol), 10% palladium on activated carbon (250 mg), hydrogen gas, and 96% ethanol (100 mL) as described in Example 2c. 4.30 g product was obtained (yellowish oil) which was used in 5c without any further workup.

5c—Preparation of 3-carboxypropyl 5-amino-4-oxopentanoate hydrochloride

This compound was prepared from the product of 5b (4.20 g; 13.2 mmol), 2 M HCl in diethyl ether (7.5 mL; 15 mmol), and diethyl ether (50 mL) as described in Example 1b. After evaporation of the solvent, the oily residue was triturated with diethyl ether (4×10 mL) and kept overnight in a freezer until it solidified into a pale tan solid. 1.90 g (57%) product was obtained after drying at 12 mm Hg and ambient temperature.
$^1$H NMR: (300 MHz; DMSO-d$_6$): δ 1.80 (2H, m), 2.30 (2H, t, J=7.4 Hz), 2.55 (2H, t, J=6.7 Hz), 2.82 (2H, t, J=6.4 Hz), 3.95 (2H, d, J=5.1 Hz), 4.03 (2H, t, J=6.5 Hz), 8.42 (3H, br s), 12.1 (1H, br s).
$^{13}$C NMR: (75 MHz; DMSO-d$_6$): δ 23.6, 27.0, 30.1, 34.2, 46.4, 63.3, 171.9, 173.8, 202.6.

EXAMPLE 6

Preparation of carboxyphenylmethyl 5-amino-4-oxopentanoate hydrobromide ture. After 15 min stirring, α-bromophenylacetic acid (2.15 g; 10.0 mmol) was added, followed by t-butyl alcohol (4.8 mL; 50 mmol). The reaction flask was closed with a stopper and the mixture was stirred 7 days at ambient temperature. Saturated NaHCO$_3$ solution (75 mL) and water (75 mL) was added to the reaction mixture. After separating, the aqueous layer was extracted with dichloromethane (2×15 mL). The combined organic layers were washed with water and dried (MgSO$_4$). After filtration and evaporation 2.39 g (88%) product was obtained (colourless oil).
$^1$H NMR: (200 MHz; CDCl$_3$): δ 1.46 (9H, s), 5.25 (1H, s), 7.30-7.38 (3H, m), 7.48-7.56 (2H, m).
$^{13}$C NMR: (50 MHz; CDCl$_3$): δ 27.7, 48.3, 83.0, 128.5, 128.6, 128.9, 136.2, 167.0.

6b—Preparation of t-butyl α-[5-(Boc-amino)-4-oxopentanoyloxy]-phenylacetate

This compound was prepared from 5-(Boc-amino)-4-oxopentanoic acid (1.97 g; 8.5 mmol), the product of 6a (2.35 g; 8.7 mmol), and triethylamine (0.88 g; 8.7 mmol) in ethyl acetate (30 mL) as described in Example 1a. The crude product was purified by flash chromatography on a 65×55 mm silica gel 60 column eluted with ethyl acetate-hexane (1:2) (1100 mL) collecting 18×50 mL fractions. After evaporation of fractions 3-8, 2.79 g (78%) product was obtained (amber oil).
$^1$H NMR: (200 MHz; CDCl$_3$): δ 1.39 (9H, s), 1.44 (9H, s), 2.75-2.85 (4H, m), 4.05 (2H, d, J=4.8 Hz), 5.22 (1H, br s), 5.77 (1H, s), 7.35-7.46 (5H, m).
$^{13}$C NMR: (50 MHz; CDCl$_3$): δ 27.7, 27.8, 28.3, 34.2, 50.3, 75.2, 79.8, 82.5, 127.4, 128.8, 128.9, 134.0, 155.7, 167.5, 171.6, 203.7.

6c—Preparation of carboxyphenylmethyl 5-amino-4-oxopentanoate hydrobromide

This compound was prepared from the product of 6b (2.75 g; 6.5 mmol) and 33% HBr in acetic acid (5 mL) as described in Example 1c. The crude product was purified by flash chro-

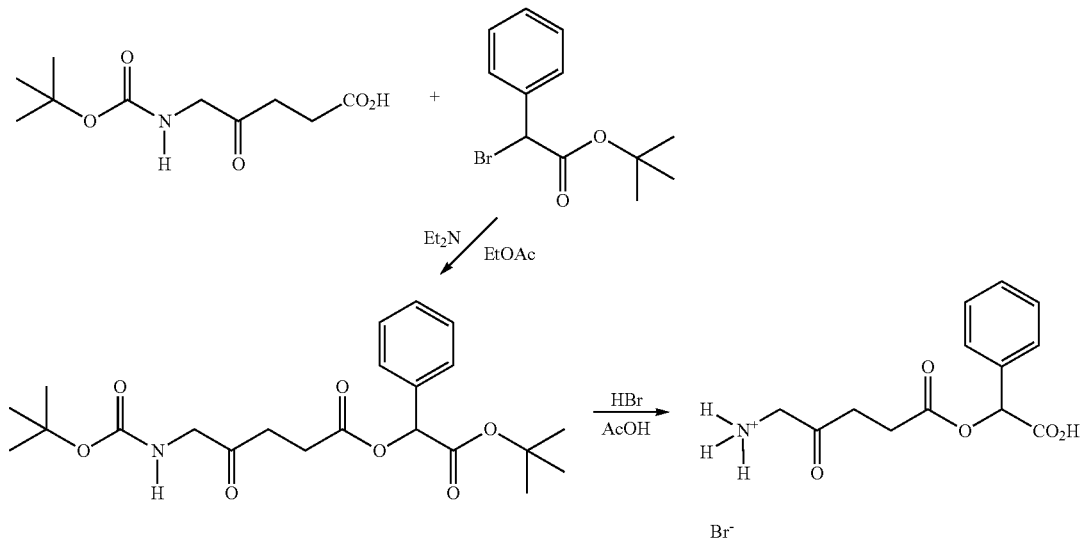

6a—Preparation of t-butyl α-bromophenylacetate

Concentrated sulphuric acid (0.55 mL; 10 mmol) was added to a stirred suspension of anhydrous MgSO$_4$ (4.8 g; 40 mmol) in dry dichloromethane (40 mL) at ambient temperamatography on a 40×55 mm silica gel 60 column eluted with 10% methanol in acetonitrile (400 mL) collecting 20×10 ml fractions. After evaporation of fractions 4-15 and vacuum-drying for 48 h at 40° C. and 0.01 mm Hg 1.60 g (71%) product was obtained (orange foam, mp 77-80° C.).

$^1$H NMR: (200 MHz; DMSO-d$_6$): δ 2.73 (2H, m), 2.85 (2H, m), 4.02 (2H, s), 5.82 (1H, s), 7.3-7.5 (5H, m), 8.13 (3H, br s).
$^{13}$C NMR: (50 MHz; DMSO-d$_6$): δ 26.8, 34.1, 46.5, 74.1, 127.4, 127.9, 128.5, 134.0, 169.4, 171.2, 202.1.

EXAMPLE 7

Preparation of (4-carboxyphenyl)methyl 5-amino-4-oxopentanoate hydrobromide

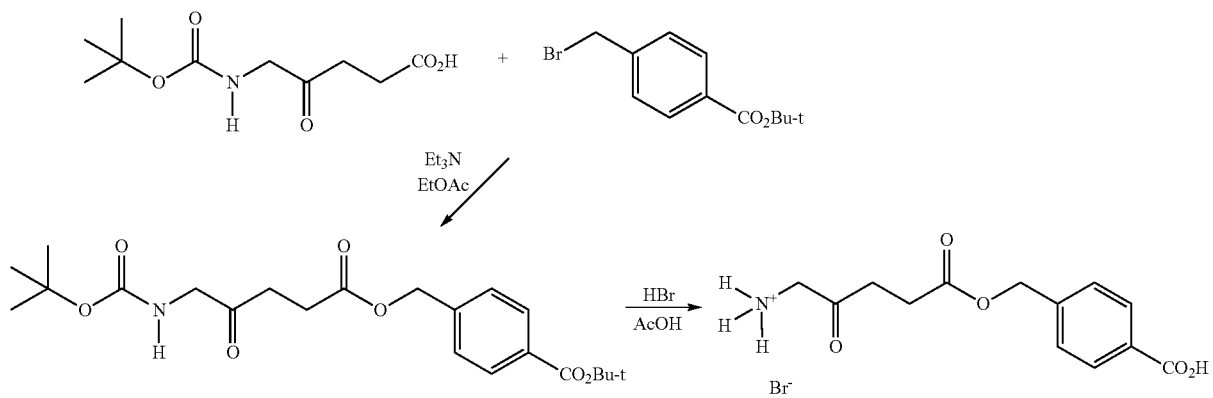

7a—Preparation of t-butyl 4-(bromomethyl)benzoate

This compound was prepared from 4-(bromomethyl)benzoic acid (2.15 g; 10.0 mmol), t-butyl alcohol (4.8 mL; 50 mmol), anhydrous MgSO$_4$ (4.8 g; 40 mmol), and concentrated sulphuric acid in dichloromethane (40 mL) as described in Example 6a. After 14 days, the mixture was worked up as described in Example 6a. 1.07 g (39%) product was obtained (white solid). The product was used in 7b without further purification.
$^1$H NMR: (200 MHz; CDCl$_3$): δ 1.59 (9H, s), 4.49 (2H, s), 7.42 (2H, d, J=8.4 Hz), 7.96 (2H, d, J=8.4 Hz).
$^{13}$C NMR: (50 MHz; CDCl$_3$): δ 28.1, 32.3, 81.2, 128.7, 129.8, 130.6, 141.9, 165.0.

7b—Preparation of t-butyl [4-[5-(Boc-amino)-4-oxopentanoyloxy]methyl]-benzoate This compound was prepared from 5-(Boc-amino)-4-oxopentanoic acid (0.81 g; 3.50 mmol), the crude product of 7a (1.00 g; 3.7 mmol), and triethylamine (0.40 g; 4.0 mmol) in ethyl acetate (15 mL) as described in Example 1a. The crude product was purified by flash chromatography on a 65×55 mm silica gel 60 column eluted with ethyl acetate-hexane (1:2) (1200 mL) collecting 16×50 mL fractions. After evaporation of fractions 6-10, 0.59 g (40%) product was obtained (colourless oil).
$^1$H NMR: (200 MHz; CDCl$_3$): δ 1.44 (9H, s), 1.59 (9H, s), 2.73 (4H, s), 4.05 (2H, d, J=5.0 Hz), 4.1 (1H, br s), 5.15 (2H, s), 7.37 (2H, d, J=8.4 Hz), 7.98 (2H, d, J=8.2 Hz).
$^{13}$C NMR: (50 MHz; CDCl$_3$): δ 27.7, 28.2, 28.3, 34.3, 50.3, 81.1 (2C), 127.4 (2C), 129.6 (2C), 131.8, 140.0, 165.2, 172.0, 203.9.

7c—Preparation of (4-Carboxyphenyl)methyl 5-amino-4-oxopentanoate hydrobromide This compound was prepared from the product of 7b (0.50 g; 1.2 mmol) and 33% HBr in acetic acid (2 mL) as described in Example 1c. Addition of HBr gave immediate precipitation of white solids. The precipitate was triturated with hexane and diethyl ether as described in Example 1c. The residue was vacuum-dried for 48 h at 40° C. and 0.01 mm Hg. 0.37 g (88%) product was obtained (white powder, mp 198-200° C. (dec.)).
$^1$H NMR: (200 MHz; DMSO-d$_6$): δ 2.68 (2H, t, J=6.2 Hz), 2.88 (2H, t, J=6.2 Hz), 4.03 (2H, s), 5.19 (2H, s), 7.49 (2H, d, J=8.0 Hz), 7.96 (2H, d, J=8.4 Hz), 8.13 (3H, br s).
$^{13}$C NMR: (50 MHz; DMSO-d$_6$): δ 27.0, 34.2, 46.6, 64.8, 127.3, 129.2, 130.1, 140.8, 166.8, 171.6, 202.4.

EXAMPLES 8 TO 15

Preparation of straight-chained carboxyalkyl 5-amino-4-oxopentanoate hydrochlorides General structure of straight-chained carboxyalkyl 5-amino-4-oxopentanoate hydrochlorides described in Examples 8 to 15:

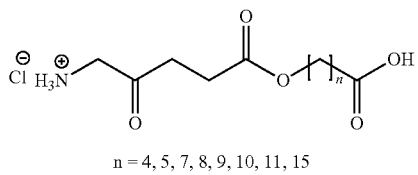

n = 4, 5, 7, 8, 9, 10, 11, 15

General procedures used for the preparation of the compounds in Examples 8 to 15:

Procedure a Preparation of Benzyl Esters Using Carbodiimides

A solution of N,N'-dicyclohexylcarbodiimide (DCC) or N,N'-diisopropylcarbodiimide in dry dichloromethane (10 mL) was added drop-wise via a syringe to a stirred solution of the carboxylic acid, benzyl alcohol or 2,2,2-trichloroethanol, and 4-pyrrolidinylpyridine in dry dichloromethane (40 mL) under argon. After stirring for one to two days at ambient temperature, the mixture was vacuum filtered and the residue was washed with a little dichloromethane. The solvent was evaporated off and the residue was vacuum dried at 50° C. (bath temperature) and 0.014 mm Hg using a Kugelrohr apparatus to remove excess benzyl alcohol.

Procedure B Preparation of Benzyl Esters Using Azeotropic Distillation

A mixture of the carboxylic acid, benzyl alcohol, and p-toluenesulphonic acid in toluene was refluxed overnight through a Dean-Stark trap. After cooling to ambient temperature, the mixture was washed with saturated NaHCO$_3$ solution (1×15 mL) and saturated NaCl (1×15 mL). After drying (MgSO$_4$), filtration, and evaporation, the residue was vacuum dried at 50° C. (bath temperature) and 0.014 mm Hg using a Kugelrohr apparatus.

Procedure C Coupling esters to N-protected 5-ALA derivatives

ω-bromoalkanoates and caesium 5-(Cbz-amino)-4-oxopentanoate

Benzyl ω-bromoalkanoate, caesium 5-(Cbz-amino)-4-oxopentanoate, and NaI (10 mg) in dry DMSO (25 mL) was heated to 100° C. (bath temperature) under argon overnight. The mixture was cooled to ambient temperature, diluted with water (150 mL), and extracted with diethyl ether (5×25 mL). The combined ether solutions were washed with water (2×10 mL), saturated NaCl solution (1×10 mL), and dried (MgSO$_4$). After filtration and evaporation, the residue was purified by flash chromatography on a silica gel 60 column eluted with ethyl acetate-hexane (1:1). Fractions containing the product were evaporated to isolate the protected 5-ALA ester.

Procedure D Coupling Esters to N-Protected 5-ALA Derivatives

ω-hydroxyalkanoates and 5-(Cbz-amino)-4-oxopentanoic Acid

A solution of N,N'-dicyclohexylcarbodiimide (DCC) in dry dichloromethane (10 mL) was added to a stirred solution of the w-hydroxyalkanoate, 5-(Cbz-amino)-4-oxopentanoic acid, and 4-pyrrolidinylpyridine (50 mg) in dry dichloromethane (25 mL) under argon. After the mixture was stirred at ambient temperature for 1-3 days, it was vacuum filtered. The filtrate was evaporated and the residue was purified by flash chromatography on a silica gel 60 column eluted with ethyl acetate-hexane (1:1). Fractions containing the product were evaporated to isolate the protected 5-ALA ester.

Procedure E Coupling Esters to N-Protected 5-ALA Derivatives trichloroethyl ω-hydroxyalkanoates and 5-(Boc-amino)-4-oxopentanoic acid A solution of N,N'-dicyclohexylcarbodiimide (DCC, 2.41 g; 14.1 mmol) in dry dichloromethane (15 mL) was added drop-wise to a stirred solution of 2,2,2-trichloroethyl w-hydroxyalkanoate, 5-(Boc-amino)-4-oxopentanoic acid, and pyridine in dry dichloromethane cooled to 0° C. (bath temperature) under argon. After stirring for one hour at 0° C., the mixture was stirred at ambient temperature overnight. The reaction mixture was vacuum filtered and acetic acid (3 mL) was added to the filtrate. After standing 30 min, the mixture was re-filtered and the filtrate was diluted with diethyl ether (150 mL). The solution was washed with 1 M HCl (3×25 mL), water (3×25 mL), saturated NaHCO$_3$ solution (2×25 mL), and saturated NaCl solution (1×25 mL). After drying (MgSO$_4$), filtration, and evaporation, the residue was purified by flash chromatography on a silica gel 60 column eluted with ethyl acetate-hexane. Fractions containing the product were evaporated to give the product.

EXAMPLE 8

Preparation of 4-carboxybutyl 5-amino-4-oxopentanoate hydrochloride

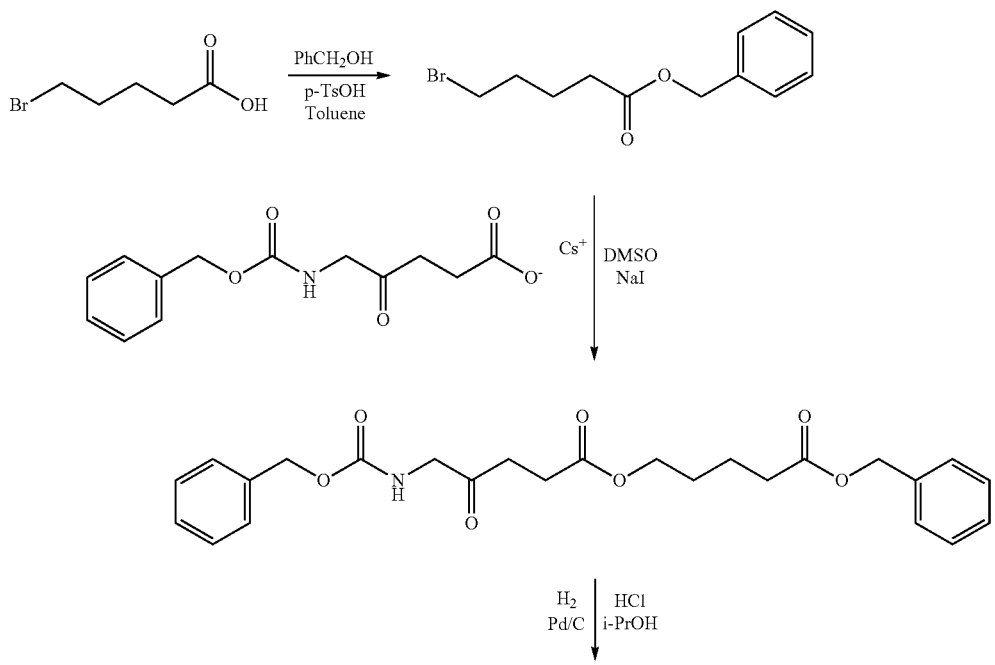

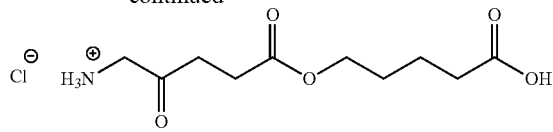

8a—Preparation of benzyl 5-bromopentanoate

This compound was prepared from 5-bromopentanoic acid (1.81 g; 10.0 mmol), benzyl alcohol (1.62 g; 15.0 mmol), and p-toluenesulphonic acid (50 mg) in toluene (100 mL) using Procedure B. 2.60 g (96%) product was obtained (clear oil). The product was used in 8c without further purification.

$^1$H NMR (200 MHz; CDCl$_3$): δ 1.8-1.9 (4H, m, J=7.2 Hz), 2.39 (2H, t, J=7.2 Hz); 3.39 (2H, t, J=6.4 Hz); 5.12 (2H, s), 7.35 (5H, s) ppm.

$^{13}$C NMR (50 MHz; CDCl$_3$): δ 23.5, 31.9, 32.9, 33.2, 66.2, 128.1, 128.2, 128.4, 135.8, 172.7 ppm.

8b—Preparation of caesium 5-(Cbz-amino)-4-oxopentanoate 5-(Cbz-amino)-4-oxopentanoic acid (2.66 g; 10.0 mmol) was added to a stirred solution of caesium carbonate (1.64 g; 5.0 mmol) in de-ionized water (40 mL). After the evolution of CO$_2$ ceased, the mixture was frozen with liquid nitrogen and freeze-dried overnight. 4.2 g (~100%) product was obtained (pale tan solid). The product was used in 8c without further purification.

8c—Preparation of 4-(benzyloxycarbonyl)butyl 5-(Cbz-amino)-4-oxopentanoate

This compound was prepared from the products of 8a (0.73 g; 2.7 mmol) and 8b (1.0 g; 2.5 mmol) according to Procedure C. The crude product was purified on a 75×45 mm silica gel 60 column eluted with ethyl acetate-hexane (1:1) (1000 mL) collecting 13×50 mL fractions. Fractions containing the product (5-8) were collected, and after evaporation 0.82 g (72%) product was obtained (yellowish solid, mp 53-56° C.).

$^1$H NMR (200 MHz; DMSO-d$_6$): δ 1.58 (4H, br s), 2.3-2.5 (4H, overlapped t), 2.69 (2H, t, J=6 Hz), 3.89 (2H, d, J=5.8 Hz), 3.99 (2H, br s); 5.04 (2H, s), 5.09 (2H, s), 7.36 (10H, s) ppm.

$^{13}$C NMR (50 MHz; DMSO-d$_6$): δ 20.9, 23.6, 27.2, 32.8, 33.6, 49.6, 63.4, 65.2, 65.3, 127.5, 127.6, 127.7, 127.8, 128.1, 128.2, 136.0, 136.8, 156.2, 171.9, 172.3, 205.3 ppm.

8d—Preparation of 4-carboxybutyl 5-amino-4-oxopentanoate hydrochloride

A stirred mixture of the product from 8c (0.70 g; 1.54 mmol), 12 M HCl (0.13 mL; 1.54 mmol), 10% Pd/C (Degussa type E101 NE/W) (100 mg), and 2-propanol (25 mL) was hydrogenated at ambient temperature and 4 bars pressure overnight. The mixture was filtered through a Celite® 545 pad; the filtrate was evaporated and the residue was triturated with dry diethyl ether (3×5 mL). After drying of the residue at ambient temperature and 0.01 mm Hg, 0.38 g (97%) product was obtained (white solid).

$^1$H NMR (200 MHz; DMSO-d$_6$): δ 1.4-1.7 (4H, m), 2.25 (2H, t, J=6.4 Hz), 2.55 (2H, t, J=6.4 Hz), 2.82 (2H, t, J=6.4 Hz), 3.9-4.1 (4H, m), 8.43 (3H, s) ppm.

$^{13}$C NMR (50 MHz; DMSO-d$_6$): δ 20.9, 23.5, 27.0, 30.0, 34.2, 46.4, 63.6, 171.8, 173.6, 202.3 ppm.

EXAMPLE 9

Preparation of 5-carboxypentyl 5-amino-4-oxopentanoate hydrochloride

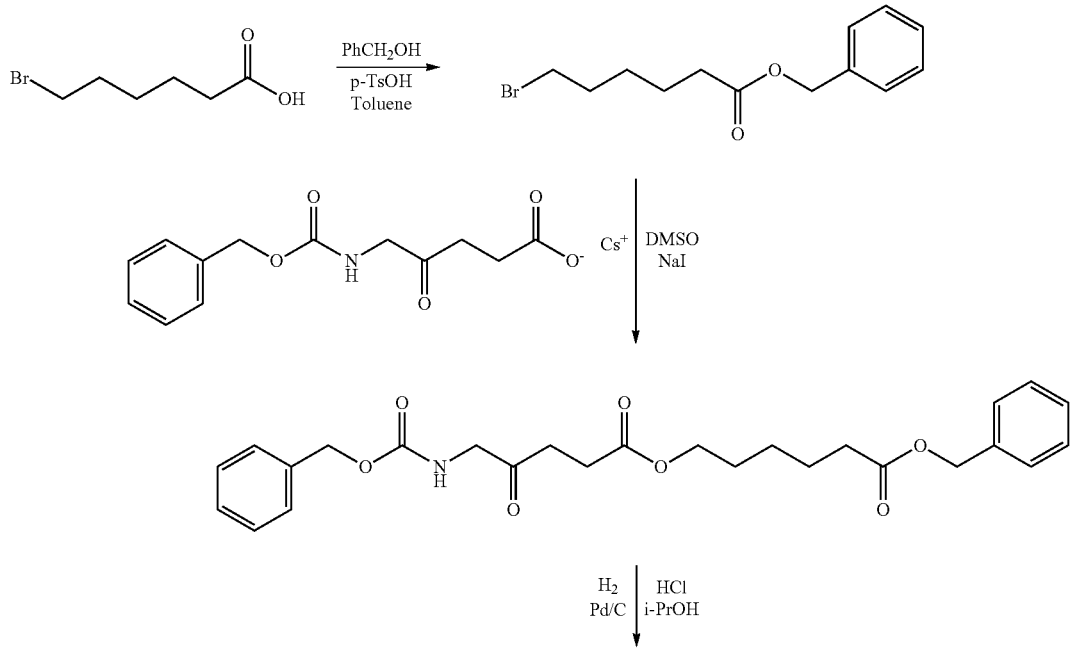

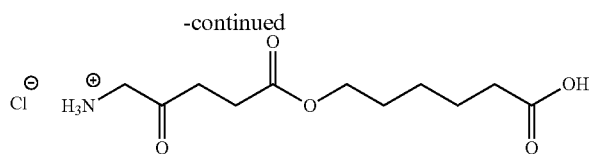

9a—Preparation of benzyl 6-bromohexanoate

This compound was prepared from 6-bromohexanoic acid (1.95 g; 10.0 mmol), benzyl alcohol (1.62 g; 15.0 mmol), and p-toluenesulphonic acid (50 mg) in toluene (100 mL) using Procedure B. 2.80 g (98%) product was obtained (clear oil). The product was used in 9b without further purification.

$^1$H NMR (200 MHz; CDCl$_3$): δ 1.4-1.5 (2H, m, J=6.8 Hz), 1.6-1.7 (2H, m, J=7.2 Hz), 1.8-1.9 (2H, m, J=7.4 Hz), 2.37 (2H, t, J=7.4 Hz); 3.38 (2H, t, J=6.6 Hz); 5.12 (2H, s), 7.35 (5H, s) ppm.

$^{13}$C NMR (50 MHz; CDCl$_3$): δ 24.0, 27.7, 32.3, 33.4, 34.0, 66.1, 128.1, 128.4, 135.9, 173.0 ppm.

9b—Preparation of 5-(benzyloxycarbonyl)pentyl 5-(Cbz-amino)-4-oxopentanoate

This compound was prepared from the product of 9a (0.77 g; 2.7 mmol) and 8b (1.0 g; 2.5 mmol) according to Procedure C. The reaction time was 2 days. The crude product was purified on a 75×45 mm silica gel 60 column eluted with ethyl acetate-hexane (1:1) (1000 mL) collecting 14×50 mL fractions. Fractions containing the product (5-7) were collected, and after evaporation 0.52 g (44%) product was obtained (amber oil that solidified to a waxy solid on standing in the freezer).

$^1$H NMR (200 MHz; DMSO-d$_6$): δ 1.25-1.38 (2H, m), 1.45-1.6 (4H, m), 2.36 (2H, t, J=7.2 Hz), 2.47 (2H, t, J=6.4 Hz), 2.69 (2H, t, J=6.2 Hz), 3.85-4.1 (4H, overlapped d and t, J=6 and 6.4 Hz), 5.04 (2H, s), 5.09 (2H, s), 7.36 (10H, s) ppm.

$^{13}$C NMR (50 MHz; DMSO-d$_6$): δ 24.0, 24.7, 27.2, 27.6, 33.2, 33.6, 49.6, 63.6, 65.2, 65.3, 127.5, 127.6, 127.7, 127.8, 128.1, 128.2, 136.1, 136.8, 156.2, 171.9, 172.4, 205.3 ppm.

9c—Preparation of 5-carboxypentyl 5-amino-4-oxopentanoate hydrochloride

This compound was prepared from the product of 9b (0.45 g; 0.96 mmol), 12 M HCl (0.08 mL; 0.96 mmol), 10% Pd/C (100 mg), hydrogen gas, and 2-propanol (25 mL) using the procedure in Example 8d. 0.20 g (77%) product was obtained (white solid).

$^1$H NMR (200 MHz; DMSO-d$_6$): δ 1.2-1.4 (2H, m), 1.4-1.7 (4H, m), 2.22 (2H, t, J=7.2 Hz), 2.55 (2H, t, J=6.4 Hz), 2.82 (2H, t, J=6.2 Hz), 3.9-4.1 (4H, m), 8.41 (3H, s) ppm.

$^{13}$C NMR (50 MHz; DMSO-d$_6$): δ 24.0, 24.8, 27.0, 27.7, 33.4, 34.2, 46.4, 63.8, 171.8, 174.1, 202.3 ppm.

EXAMPLE 10

Preparation of 7-carboxyheptyl 5-amino-4-oxopentanoate hydrochloride

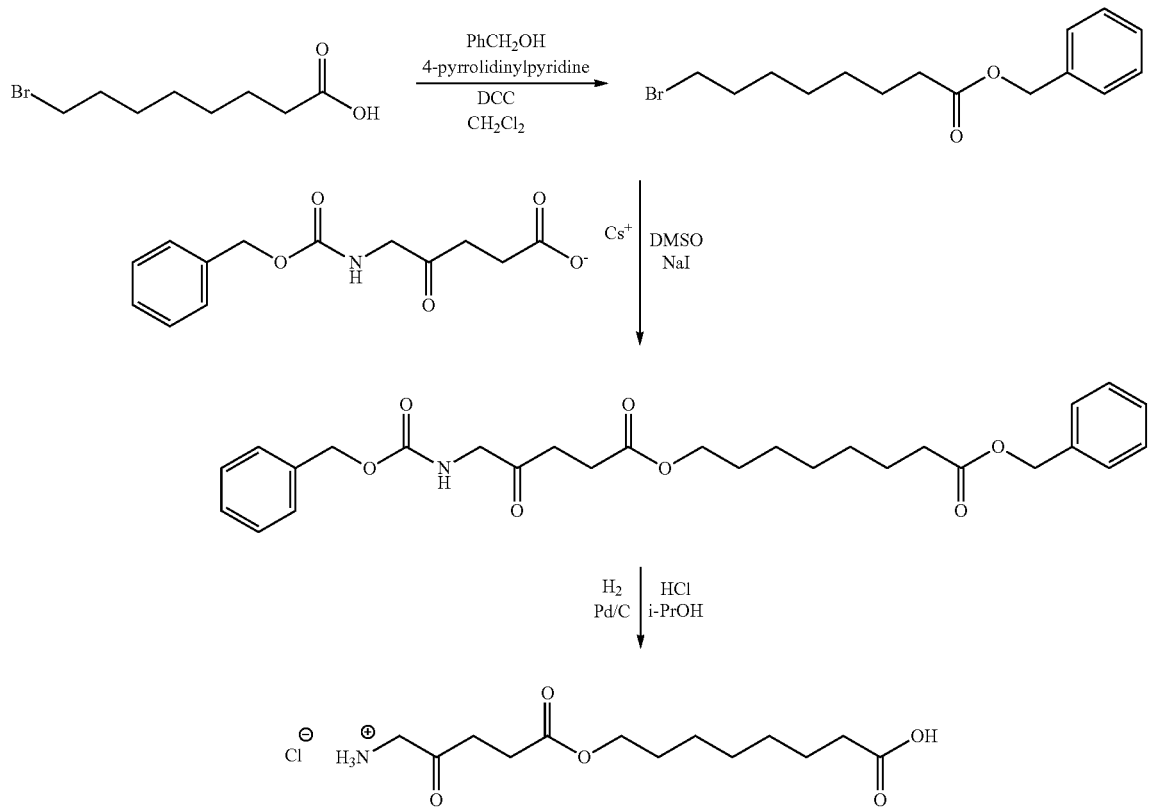

10a—Preparation of benzyl 8-bromooctanoate

This compound was prepared from 8-bromooctanoic acid (2.23 g; 10.0 mmol), benzyl alcohol (1.19 g; 11.0 mmol), N,N'-dicyclohexylcarbodiimide (DCC, 2.27 g; 11.0 mmol), and 4-pyrrolidinylpyridine (50 mg) in dry dichloromethane (50 mL) using Procedure A. 3.14 g (100%) product was obtained (clear oil that eventually solidified on standing).

$^1$H NMR (200 MHz; CDCl$_3$): δ 1.33 (6H, br s), 1.6-1.7 (2H, m), 1.75-1.9 (2H, m), 2.35 (2H, t, J=7.8 Hz); 3.38 (2H, t, J=6.8 Hz); 5.11 (s, 2H), 7.35 (s, 5H) ppm.

$^{13}$C NMR (50 MHz; CDCl$_3$): δ 24.8, 27.9, 28.3, 28.9, 32.6, 33.8, 34.2, 66.0, 128.1, 128.4, 136.0, 173.3 ppm.

10b—Preparation of 7-(benzyloxycarbonyl)heptyl 5-(Cbz-amino)-4-oxopentanoate This compound was prepared from the product of 10a (0.79 g; 2.5 mmol) and 8b (1.0 g; 2.5 mmol) according to Procedure C. The reaction time was 2 days. The crude product was purified on a 80×45 mm silica gel 60 column eluted with ethyl acetate-hexane (1:1) (1000 mL) collecting 13×50 mL fractions. Fractions containing the product (3-6) were collected, and after evaporation 0.83 g (67%) product was obtained (amber oil that solidified to a waxy solid on standing in the freezer, mp 52-54° C.).

$^1$H NMR (200 MHz; DMSO-d$_6$): δ 1.26 (6H, br s), 1.53 (4H, br s), 2.34 (2H, t, J=7.2 Hz), 2.48 (2H, t, J=5.8 Hz), 2.69 (2H, t, J=6.4 Hz), 3.38 (1H, t, J=6.6 Hz), 3.89 (2H, d, J=6 Hz), 3.98 (2H, t, J=6.6 Hz), 5.04 (2H, s), 5.08 (2H, s), 7.35 (10H, s) ppm.

$^{13}$C NMR (50 MHz; DMSO-d$_6$): δ 24.3, 25.1, 26.3, 27.2, 27.9, 33.4, 33.7, 49.6, 63.8, 65.1, 65.3, 127.4, 127.7, 128.2, 136.1, 136.8, 156.1, 171.8, 172.5, 205.2 ppm.

10c—Preparation of 7-carboxyheptyl 5-amino-4-oxopentanoate hydrochloride

This compound was prepared from the product of 10b (0.70 g; 1.4 mmol), 12 M HCl (0.12 mL; 1.4 mmol), 10% Pd/C (100 mg), hydrogen gas, and 2-propanol (25 mL) using the procedure in Example 8d. 0.30 g (70%) product was obtained (white solid).

$^1$H NMR (200 MHz; DMSO-d$_6$): δ 1.28 (6H, s), 1.4-1.7 (4H, m), 2.20 (2H, t, J=7 Hz), 2.55 (2H, t, J=6.2 Hz), 2.81 (2H, t, J=6.2 Hz), 3.9-4.1 (4H, m), 8.42 (3H, s) ppm.

$^{13}$C NMR (50 MHz; DMSO-d$_6$): δ 24.3, 25.1, 27.0, 27.9, 28.2, 28.3, 33.6, 34.2, 46.4, 63.9, 171.8, 174.2, 202.3 ppm.

EXAMPLE 11

Preparation of 8-carboxyoctyl 5-amino-4-oxopentanoate hydrochloride

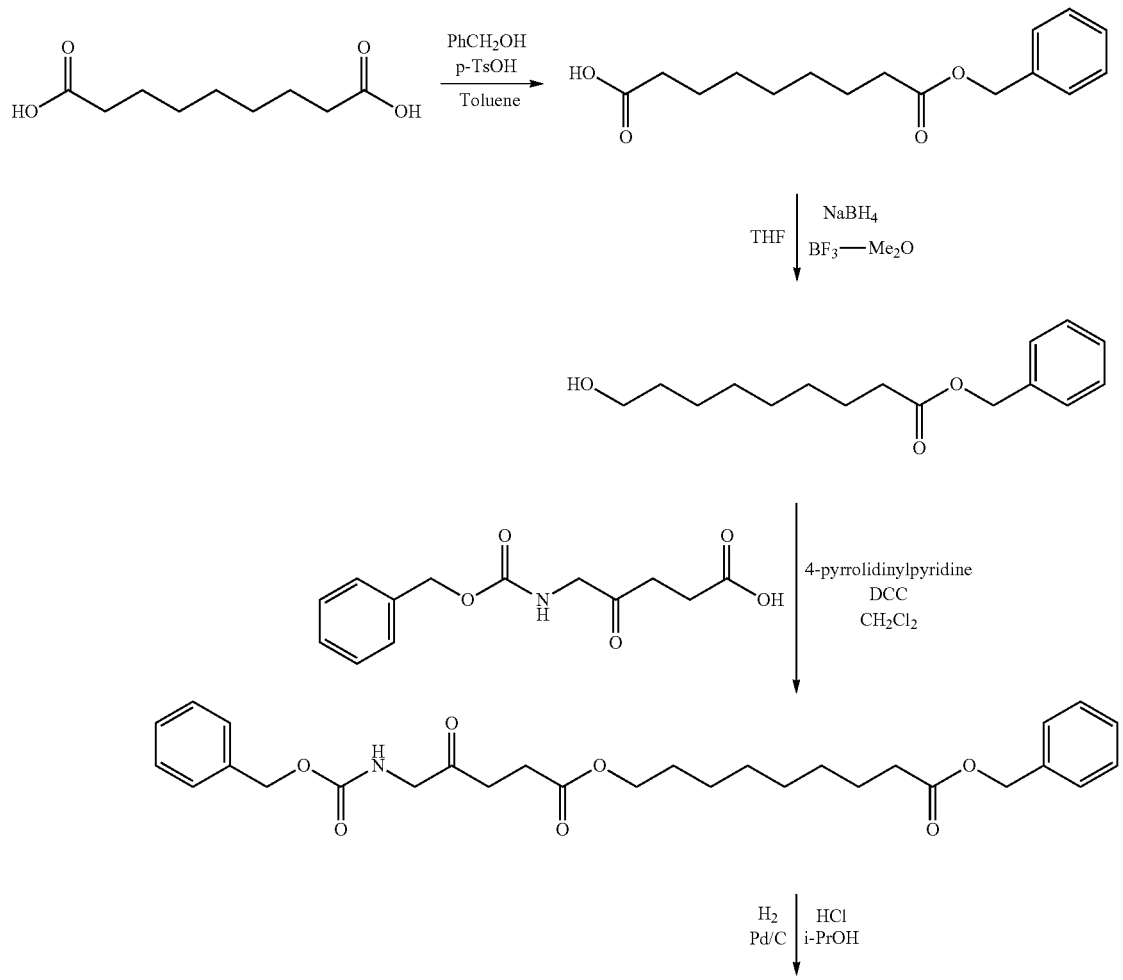

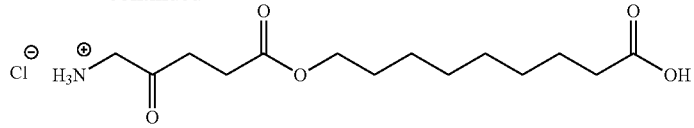

11a—Preparation of benzyl hydrogen nonanedioate

A stirred mixture of nonanedioic acid (18.8 g; 0.10 mol), benzyl alcohol (10.8 g; 0.10 mol), and p-toluenesulphonic acid (0.2 g) in toluene (200 mL) was refluxed through a Dean-Stark trap overnight. The mixture was cooled to ambient temperature and extracted with 10% aqueous N-methyl-D-glucamine (4×25 mL). The last extract was a milky emulsion. The first three extracts were combined, acidified with 1 M HCl (50 mL), and filtered to give recovered nonanedioic acid (3.8 g). The emulsion was acidified with 1 M HCl and allowed to separate overnight. The organic layer was evaporated and the residue dissolved in hexane (200 mL) and diethyl ether (50 mL). The solution was extracted with 10% N-methyl-D-glucamine (2×50 mL) (emulsions broken by adding a little ethanol). The organic solution was washed with water (1×25 mL) and the combined aqueous solution was acidified with 1 M HCl (150 mL). After extraction with dichloromethane-tetrahydrofuran (4:1) (5×10 mL), the combined extracts were dried ($Na_2SO_4$), filtered, and evaporated. 13.0 g (47%) product was obtained (oil that solidified on standing).

$^1$H NMR (200 MHz; $CDCl_3$): δ 1.31 (6H, br s), 1.5-1.8 (4H, m), 2.25-2.4 (4H, m); 5.11 (s, 2H), 7.34 (5H, s), 10.4 (1H, br s) ppm.

$^{13}$C NMR (50 MHz; $CDCl_3$): δ 24.6, 28.8, 34.0, 34.2, 66.1, 128.1, 128.4, 136.0, 173.5, 179.9 ppm.

11b—Preparation of benzyl 9-hydroxynonanoate

The product from 11a (12.9 g; 46.3 mmol) was added in portions to a stirred mixture of sodium borohydride (1.70 g; 45.0 mmol) in dry tetrahydrofuran (25 mL). After the evolution of hydrogen subsided, a solution of boron trifluoride dimethyl etherate (4.6 mL; 5.7 g; 50 mmol) in dry tetrahydrofuran (15 mL) was added drop-wise. The exothermic reaction was moderated with a cold water bath. After stirring 4 h at ambient temperature, the reaction mixture was hydrolyzed with cold water (20 mL). The mixture was separated and the organic phase was evaporated; the residue was mixed with water (20 mL) and dichloromethane (70 mL) to give an emulsion that separated on standing overnight. The organic layer was washed with water (4×15 mL) until the washings were neutral to pH paper. Following drying ($Na_2SO_4$), filtration, and evaporation 11.95 g (98%) product was obtained (oil).

$^1$H NMR (200 MHz; $CDCl_3$): δ 1.30 (8H, br s), 1.4-1.75 (4H, m), 2.34 (2H, t, J=7.6); 3.62 (2H, t, J=6.6 Hz), 5.10 (2H, s), 7.34 (5H, s) ppm.

$^{13}$C NMR (50 MHz; $CDCl_3$): δ 24.9, 25.6, 29.0, 29.1, 32.6, 34.3, 63.0, 66.0, 128.0, 128.4, 136.0, 173.6 ppm.

11c—Preparation of 8-(benzyloxycarbonyl)octyl 5-(Cbz-amino)-4-oxopentanoate

This compound was prepared from the product from 11 b (1.1 g; 4.2 mmol), 5-(Cbz-amino)-4-oxopentanoic acid (1.0 g; 3.8 mmol), 4-pyrrolidinylpyridine (60 mg), and N,N'-dicyclohexylcarbodiimide (DCC, 0.87 g; 4.2 mmol) in dichloromethane (35 mL) according to Procedure D. The reaction time was 3 days. The crude product was purified on a 85×45 mm silica gel 60 column eluted with ethyl acetate-hexane (1:1) (1000 mL) collecting 14×50 mL fractions. Fractions containing the product (4-7) were evaporated and 1.5 g (77%) product was obtained.

$^1$H NMR (200 MHz; DMSO-$d_6$): δ 1.24 (8H, br s), 1.54 (4H, overlapped t, J=6.2 Hz), 2.34 (2H, t, J=7.2 Hz), 2.48 (2H, t, J=6.2 Hz), 2.69 (2H, t, J=6.2 Hz), 3.89 (2H, d, J=6 Hz), 3.97 (2H, t, J=6.6 Hz), 5.04 (2H, s), 5.08 (2H, s), 7.35 (10H, s) ppm.

$^{13}$C NMR (50 MHz; DMSO-$d_6$): δ 23.6, 24.3, 25.0, 27.2, 27.9, 33.3, 33.6, 49.6, 63.8, 65.1, 65.3, 127.5, 127.6, 127.7, 128.1, 128.2, 136.1, 136.8, 156.2, 171.9, 172.5, 205.3 ppm.

11d—Preparation of 8-carboxyoctyl 5-amino-4-oxopentanoate hydrochloride

This compound was prepared from the product of 11c (1.4 g; 2.7 mmol), 12 M HCl (0.25 mL; 3.0 mmol), 10% Pd/C (100 mg), hydrogen gas, and 2-propanol (25 mL) using the procedure in Example 8d. 0.54 g (62%) product was obtained (white solid).

$^1$H NMR (200 MHz; DMSO-$d_6$): δ 1.1-1.7 (12H, m), 2.20 (2H, t, J=7.4 Hz), 2.54 (2H, t, J=6.4 Hz), 2.81 (2H, t, J=6.4 Hz), 3.9-4.1 (4H, m), 8.40 (3H, s) ppm.

$^{13}$C NMR (50 MHz; DMSO-$d_6$): δ 24.4, 25.1, 27.0, 28.0, 28.4, 28.5, 33.5, 34.2, 46.4, 63.9, 171.8, 174.2, 202.3 ppm.

EXAMPLE 12

Preparation of 9-carboxynonyl 5-amino-4-oxopentanoate hydrochloride

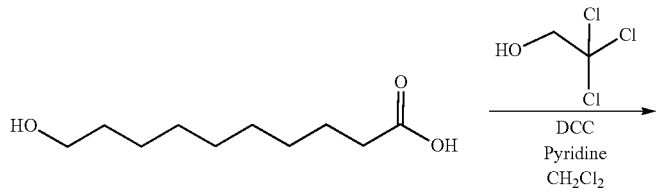

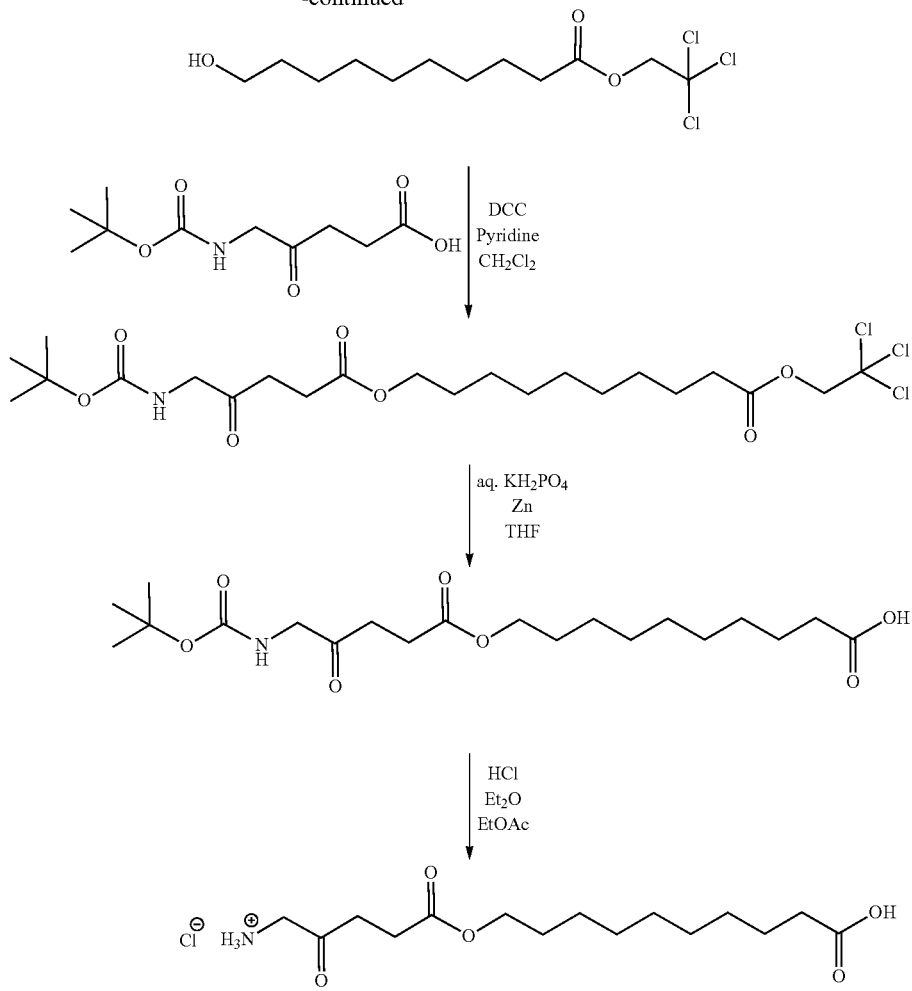

12a—Preparation of 2,2,2-trichloroethyl 10-hydroxydecanoate

A solution of N,N'-dicyclohexylcarbodiimide (DCC, 2.41 g; 14.1 mmol) in dry dichloromethane (15 mL) was added drop-wise to a stirred solution of 10-hydroxydecanoic acid (1.88 g; 10.0 mmol), 2,2,2-trichloroethanol (6.13 g; 41.0 mmol), and pyridine (4.1 mL) in dry dichloromethane (35 mL) cooled to 0° C. (bath temperature) under argon. After stirring one hour at 0° C., the mixture was stirred at ambient temperature overnight. The reaction mixture was vacuum filtered and acetic acid (3 mL) was added to the filtrate. After standing 30 min, the mixture was refiltered and the filtrate was diluted with diethyl ether (150 mL). The solution was washed with 1 M HCl (3×25 mL), water (3×25 mL), saturated NaHCO$_3$ solution (2×25 mL), and saturated NaCl solution (1×25 mL). After drying (MgSO$_4$), filtration, and evaporation, the residue was purified by flash chromatography on a 170×25 mm silica gel 60 column eluted with ethyl acetate-hexane (1:1), collecting 12×25 mL fractions. Fractions 3-5 were evaporated and the residue was vacuum dried at 50° C. and 0.05 mm Hg on a Kugelrohr apparatus to remove excess 2,2,2-trichloroethanol. 2.1 g (66%) product was obtained (colorless oil).

$^1$H NMR (200 MHz; CDCl$_3$): δ 1.32 (10H, br s), 1.4-1.8 (5H, m), 2.47 (2H, t, J=7.2 Hz); 3.63 (2H, t, J=6.4 Hz), 4.74 (2H, s) ppm.

$^{13}$C NMR (50 MHz; CDCl$_3$): δ 24.7, 25.6, 29.0, 29.1, 29.28, 29.32, 32.6, 33.9, 63.0, 73.8, 95.0, 172.1 ppm.

12b—Preparation of 2,2,2-trichloroethyl 10-[5-(Boc-amino)-4-oxopentanoyloxy]decanoate This compound was prepared from 5-(Boc-amino)-4-oxopentanoic acid (1.00 g; 4.3 mmol), the product from 12a (1.37 g; 4.3 mmol), N,N'-dicyclohexylcarbodiimide (DCC, 1.03 g; 5.0 mmol), and pyridine (2.0 mL) in dichloromethane (40 mL) using Procedure E. The crude product was purified on a 100×50 mm silica gel 60 column eluted with ethyl acetate-hexane (1:2), collecting 16×50 mL fractions. From evaporation of fractions 4-9 gave 1.6 g (71%) product was obtained (yellowish oil).

$^1$H NMR (200 MHz; CDCl$_3$): δ 1.31 (10H, br s), 1.44 (9H, s), 1.5-1.8 (4H, m), 2.46 (2H, t, J=7.2 Hz), 2.6-2.8 (4H, m), 4.0-4.1 (4H, m), 4.74 (2H, s) ppm.

$^{13}$C NMR (50 MHz; CDCl$_3$): δ 24.7, 25.7, 25.8, 27.8, 28.3, 28.5, 28.9, 29.2, 29.3, 32.7, 33.9, 50.3, 64.9, 73.8, 95.0, 171.9, 172.3, 204 ppm.

12c—Preparation of 9-carboxynonyl 5-(Boc-amino)-4-oxopentanoate

One molar potassium dihydrogen phosphate (KH$_2$PO$_4$) solution (4.0 mL; 4.0 mmol) followed by zinc powder (2.0 g;

30 mmol) was added to a stirred solution of the product from 12b (1.50 g; 2.8 mmol) in tetrahydrofuran (25 mL). After stirring 18 h at ambient temperature, a new portion of 1 M KH$_2$PO$_4$ solution (5 mL) and zinc (2.0 g; 30 mmol) was added. Additional 1 M KH$_2$PO$_4$ solution (25 mL) was added after 5 h and the mixture was stirred overnight at ambient temperature. The mixture was vacuum filtered and the residue was washed with ethyl acetate. Ethyl acetate in the filtrate was evaporated off and the aqueous solution was extracted with dichloromethane (4×5 mL). The combined extracts were dried (Na$_2$SO$_4$), filtered, and evaporated. 1.04 g (93%) product was obtained (pale yellow waxy solid).

$^1$H NMR (200 MHz; CDCl$_3$): δ 1.30 (10H, br s), 1.44 (9H, s), 1.5-1.7 (4H, m), 2.34 (2H, t, J=7.4 Hz), 2.6-2.8 (4H, m), 4.0-4.1 (4H, m) ppm.

$^{13}$C NMR (50 MHz; CDCl$_3$): δ 24.7, 25.7, 25.8, 27.8, 28.3, 28.5, 29.0, 29.1, 29.2, 29.3, 32.6, 34.0, 50.3, 65.0; 172.4, 179.1 ppm.

12d—Preparation of 9-carboxynonyl 5-amino-4-oxopentanoate hydrochloride

A 1.0 M solution of HCl in diethyl ether (7.0 mL; 7.0 mmol) was added to a stirred solution of the product from 12c (1.0 g; 2.5 mmol) in ethyl acetate (10 mL) at ambient temperature under argon. After 7 h, the excess solvent was evaporated and the residue was triturated with diethyl ether (4×5 mL). The residue was dried overnight at 40° C. and 15 mm Hg to give 0.11 g white solid. The combined ether extracts were evaporated and dissolved in 96% ethanol (25 mL) and 1 M HCl in diethyl ether (5 mL). After stirring 10 days at ambient temperature, the mixture was filtered and the residue triturated with diethyl ether as before to give 0.22 g of a second crop. LC-MS analysis indicated that the product contained ca. 30% 5-amino-4-oxopentanoic acid; the combined crops were purified by flash chromatography on a 165×25 mm silica gel 60 column eluted sequentially with acetonitrile (100 mL), 2.5% methanol in acetonitrile (500 mL), 5% methanol in acetonitrile (500 mL), then 7% methanol in acetonitrile (1000 mL), collecting 47×50 mL fractions. Fractions containing the product were evaporated and the residue was dissolved in water (10 mL). The solution was freeze-dried overnight, and 0.17 g (20%) product obtained (white solid, mp 98-102° C., softens, no sharp mp).

$^1$H NMR (200 MHz; DMSO-d$_6$): δ 1.26 (10H, br s), 1.4-1.6 (4H, m), 2.19 (2H, t, J=7.4 Hz), 2.54 (2H, t, J=6.4), 2.81 (2H, t, J=6.6 Hz), 3.9-4.1 (4H, m), 8.5 (3H, br s) ppm.

$^{13}$C NMR (50 MHz; DMSO-d$_6$): δ 24.4, 25.2, 27.0, 28.0, 28.4, 28.48, 28.54, 28.6, 33.6, 34.2, 46.4, 63.9, 171.8, 174.1, 202.3 ppm.

EXAMPLE 13

Preparation of 10-carboxydecyl 5-amino-4-oxopentanoate hydrochloride

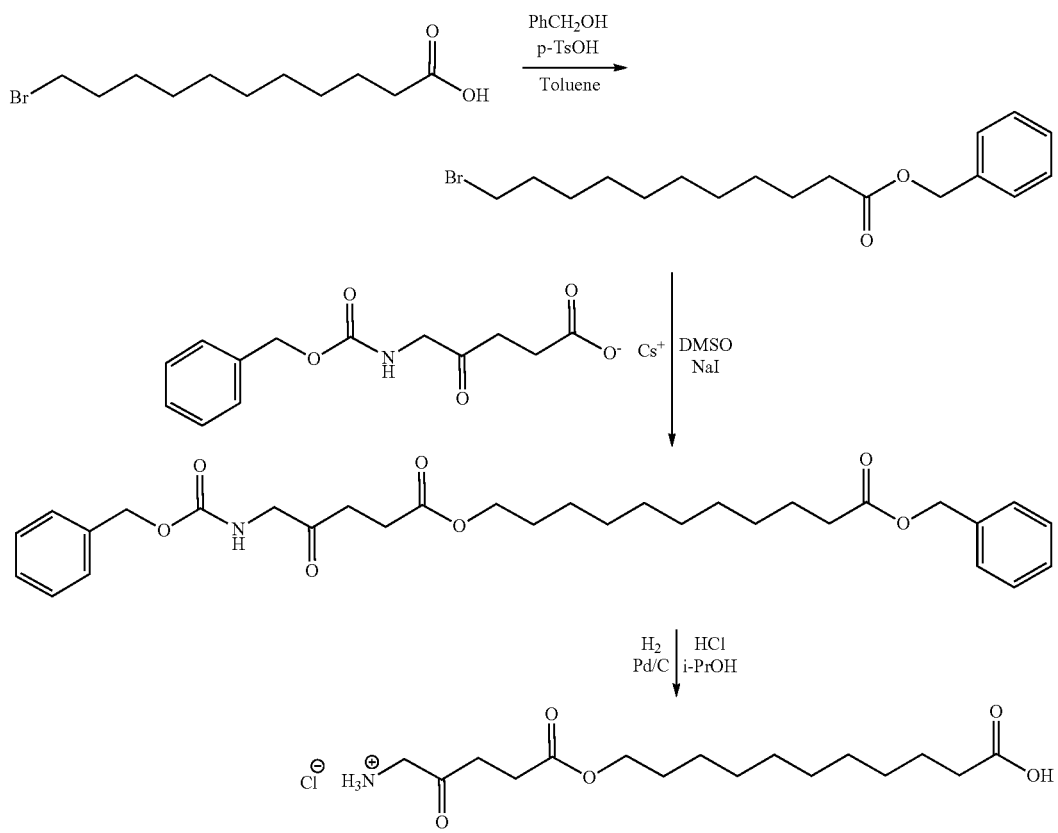

13a—Preparation of benzyl 11-bromoundecanoate

This compound was prepared from 11-bromoundecanoic acid (2.65 g; 10.0 mmol), benzyl alcohol (1.62 g; 15.0 mmol), and p-toluenesulphonic acid (50 mg) in toluene (100 mL) using Procedure B. 3.62 g product was obtained, which was used in 13b without further purification.

$^1$H NMR (200 MHz; CDCl$_3$): δ 1.27 (12H, br s), 1.6-1.7 (2H, m), 1.8-1.9 (2H, m), 2.35 (2H, t, J=7.4 Hz); 3.39 (2H, t, J=6.8 Hz); 5.11 (2H, s), 7.34 (5H, s) ppm.

$^{13}$C NMR (50 MHz; CDCl$_3$): δ 24.9, 28.1, 28.7, 28.8, 29.0, 29.1, 29.3, 32.8, 33.9, 34.3, 66.0, 128.0, 128.4, 136.0, 173.4 ppm.

13b—Preparation of 10-(benzyloxycarbonyl)decyl 5-(Cbz-amino)-4-oxopentanoate This compound was prepared from the product of 13a (0.96 g; 2.7 mmol) and 8b (1.0 g; 2.5 mmol) according to Procedure C. The crude product was purified on a 70×45 mm silica gel 60 column eluted with ethyl acetate-hexane (1:1) (1000 mL) collecting 13×50 mL fractions. The fraction containing the product (3) was evaporated and 0.69 g (47%) product was obtained (pinkish solid, mp 70-72° C.).

$^1$H NMR (200 MHz; DMSO-d$_6$): δ 1.23 (12H, br s), 1.54 (4H, br s), 2.34 (2H, t, J=7.2 Hz), 2.48 (2H, m), 2.69 (2H, t, J=6.2 Hz), 3.89 (2H, d, J=6.6 Hz), 3.98 (2H, t, J=6.2 Hz), 5.04 (2H, s), 5.08 (2H, s), 7.35 (10H, s) ppm.

$^{13}$C NMR (50 MHz; DMSO-d$_6$): δ 23.6, 24.3, 25.2, 27.2, 28.0, 28.3, 28.5, 28.7, 33.4, 33.6, 49.6, 63.8, 65.1, 65.3, 127.5, 127.6, 127.7, 128.1, 128.2, 136.1, 136.8, 156.2, 171.9, 172.5, 205.3 ppm.

13c—Preparation of 10-carboxydecyl 5-amino-4-oxopentanoate hydrochloride

This compound was prepared from the product of 13b (0.60 g; 1.1 mmol), 12 M HCl (0.09 mL; 1.1 mmol), 10% Pd/C (100 mg), hydrogen gas, and 2-propanol (25 mL) using the procedure in Example 8d. 0.20 g (51%) product was obtained (white solid).

$^1$H NMR (200 MHz; DMSO-d$_6$): δ 1.1-1.7 (16H, m), 2.19 (2H, t, J=7.4 Hz), 2.54 (2H, t, J=6.4 Hz), 2.81 (2H, t, J=6.4 Hz), 3.9-4.1 (4H, m), 8.41 (3H, s) ppm.

$^{13}$C NMR (50 MHz; DMSO-d$_6$): δ 24.4, 25.2, 27.0, 28.0, 28.4, 28.55, 28.62, 28.74, 33.6, 34.2, 46.4, 64.0, 170.6, 171.8, 202.3 ppm.

EXAMPLE 14

Preparation of 11-carboxyundecyl 5-amino-4-oxopentanoate hydrochloride

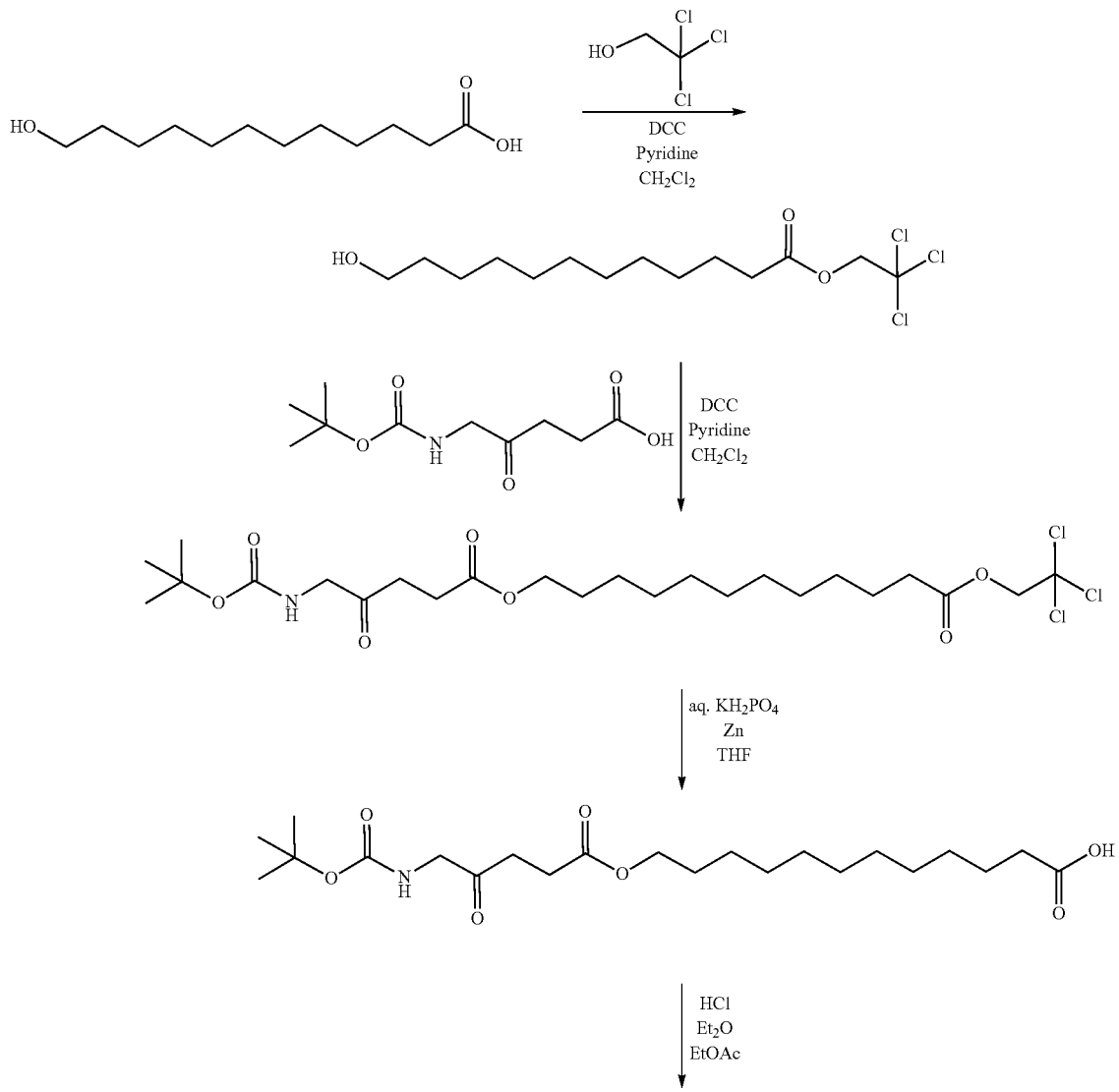

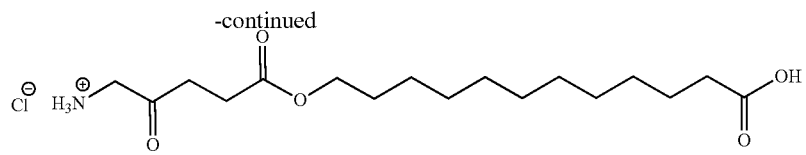

14a—Preparation of 2,2,2-trichloroethyl 12-hydroxydodecanoate

This compound was prepared from 12-hydroxydodecanoic acid (2.0 g; 9.2 mmol), 2,2,2-trichloroethanol (6.0 g; 40 mmol), N,N'-dicyclohexylcarbodiimide (DCC, 4.1 g; 20 mmol), and pyridine (5.0 mL) in dry dichloromethane (50 mL) using the procedure of Example 12a. 3.63 g (66%) product was obtained (colorless oil).

$^1$H NMR (200 MHz; CDCl$_3$): δ 1.28 (14H, br s), 1.5-1.75 (4H, m), 2.46 (2H, t, J=7.6 Hz); 3.63 (2H, t, J=6.4 Hz), 4.74 (2H, s) ppm.

$^{13}$C NMR (50 MHz; CDCl$_3$): δ 24.7, 25.7, 28.6, 29.0, 29.1, 29.2, 29.4, 32.7, 33.9, 62.9, 73.8, 95.0, 172.0 ppm.

14b—Preparation of 2,2,2-trichloroethyl 12-[5-(Boc-amino)-4-oxopentanoyloxy]dodecanoate This compound was prepared from 5-(Boc-amino)-4-oxopentanoic acid (2.0 g; 8.6 mmol), the product of 14a (3.0 g; 8.6 mmol), N,N'-dicyclohexylcarbodiimide (DCC, 2.1 g; 10.0 mmol), and pyridine (4.0 mL) in dichloromethane (75 mL) using Procedure E. The crude product was purified on a 90×50 mm silica gel 60 column eluted with ethyl acetate-hexane (1:3), collecting 13×50 mL fractions. Following evaporation of fractions 6-11, 1.44 g (30%) product was obtained (yellowish oil).

$^1$H NMR (200 MHz; CDCl$_3$): δ 1.28 (14H, br s), 1.45 (9H, s), 1.5-1.8 (4H, m), 2.46 (2H, t, J=7.4 Hz), 2.6-2.8 (4H, m), 4.0-4.1 (4H, m), 4.74 (2H, s) ppm.

$^{13}$C NMR (50 MHz; CDCl$_3$): δ 24.7, 25.8, 28.3, 28.5, 29.1, 29.2, 29.3, 29.4, 29.5, 33.9, 34.3, 50.3, 64.9, 73.8, 74.1, 95.0, 172.0, 172.3, 204.1 ppm.

14c—Preparation of 11-carboxyundecyl 5-(Boc-amino)-4-oxopentanoate

This compound was prepared from the product of 14b (1.38 g; 2.5 mmol) in tetrahydrofuran (25 mL) following the procedure in Example 12c and using the same quantities of 1 M KH$_2$PO$_4$ solution and zinc powder. Following work-up, 1.0 g (93%) product was obtained (pale yellow oil).

$^1$H NMR (200 MHz; CDCl$_3$): δ 1.28 (14H, br s), 1.44 (9H, s), 1.5-1.7 (4H, m), 2.33 (2H, t, J=7.4 Hz), 2.6-2.8 (4H, m), 4.0-4.1 (4H, m) ppm.

$^{13}$C NMR (50 MHz; CDCl$_3$): δ 24.7, 25.8, 28.3, 28.5, 29.0, 29.2, 29.3, 29.4, 32.6, 34.0, 50.3, 65.0, 172.4, 178.9, 204.3 ppm.

14d—Preparation of 11-carboxyundecyl 5-amino-4-oxopentanoate hydrochloride

A 1.0 M solution of HCl in diethyl ether (5.0 mL; 5.0 mmol) was added to a stirred solution of the product of 14c (0.95 g; 2.2 mmol) in ethyl acetate (10 mL) at ambient temperature under argon. After 5 days, the mixture was filtered and the residue was triturated with diethyl ether (2×5 mL). The residue was dried overnight at 40° C. and 15 mm Hg to give 0.11 g white solid. The combined ether extracts were evaporated. LC-MS analysis indicated that the product contained ca. 25% 5-amino-4-oxopentanoic acid; the combined crops were purified by flash chromatography on a 150×25 mm silica gel 60 column eluted sequentially with 3% methanol in acetonitrile (1000 mL), 6% methanol in acetonitrile (1000 mL), then 9% methanol in acetonitrile (2000 mL), collecting 56×50 mL fractions. Fractions containing the product were evaporated and the residue was dissolved in water (10 mL). The solution was freeze-dried overnight, and 0.06 g (7.5%) product obtained (white solid, mp 110-115° C. (softens, no sharp mp)).

$^1$H NMR (200 MHz; DMSO-d$_6$): δ 1.25 (14H, br s), 1.4-1.6 (4H, m), 2.19 (2H, t, J=7.4 Hz), 2.55 (2H, t, J=6.2 Hz), 2.80 (2H, t, J=6.4 Hz), 3.9-4.1 (4H, m), 9.1 (3H, br s) ppm.

$^{13}$C NMR (50 MHz; DMSO-d$_6$): δ 24.4, 25.2, 27.0, 28.0, 28.4, 28.5, 28.6, 28.8, 33.6, 34.1, 46.4, 64.0, 171.8, 174.2, 202.4 ppm.

EXAMPLE 15

Preparation of 15-carboxypentadecyl 5-amino-4-oxopentanoate hydrochloride

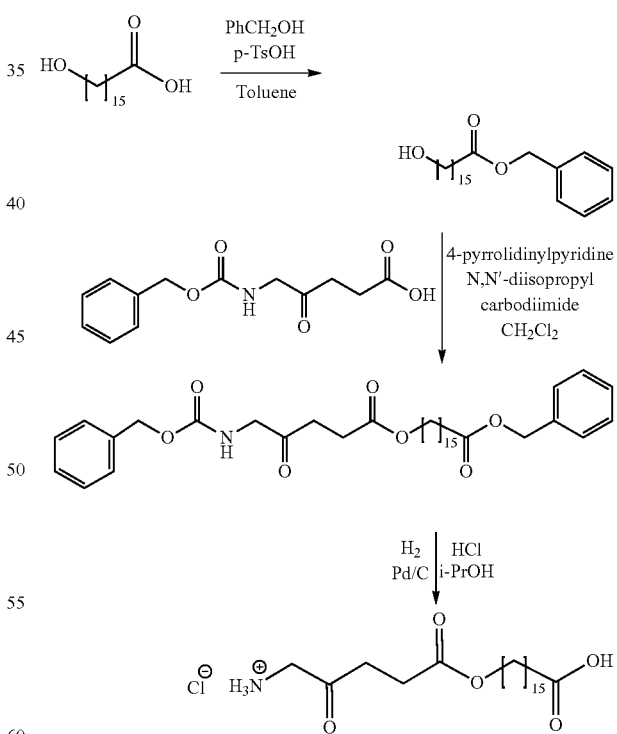

15a—Preparation of benzyl 16-hydroxyhexadecanoate

This compound was prepared from 16-hydroxyhexadecanoic acid (2.45 g; 9.0 mmol), benzyl alcohol (4.9 g; 45 mmol), and p-toluenesulphonic acid (100 mg) in toluene (100 mL) using Procedure B. 2.82 g crude product that was a 1:1 mixture of the expected product and the ester between two molecules of 16-hydroxyhexadecanoic acid was obtained. A solution of NaH (ca. 100 mg) (previously washed three times with dry hexane) in benzyl alcohol (10 g) was added to the crude product and the mixture was stirred at 100° C. (bath temperature) under argon for 3 h. After cooling to ambient temperature, the mixture was diluted with dichloromethane (75 mL) and washed with 10% aqueous citric acid solution (1×10 mL) and dried ($Na_2SO_4$). After filtration and evaporation, the residue was vacuum dried at 50° C. (bath temperature) and 0.014 mm Hg using a Kugelrohr apparatus. 2.56 g (76%) product was obtained (white solid). Proton NMR indicated that ca. 10% of the dimer ester remained.

$^1$H NMR (200 MHz; $CDCl_3$): δ 1.25 (22H, br s), 1.55-1.65 (4H, m, J=7.6 Hz), 1.9 (1H, br s), 2.35 (2H, t, J=7.4 Hz); 3.63 (2H, t, J=6.6 Hz); 5.11 (2H, s), 7.34 (5H, s) ppm.

$^{13}$C NMR (50 MHz; $CDCl_3$): δ 24.9, 25.7, 28.9, 29.1, 29.2, 29.4, 29.6, 32.8, 34.3, 63.0, 66.0, 128.0, 128.2, 128.4, 136.0, 173.6 ppm.

15b—Preparation of 15-(benzyloxycarbonyl)pentadecyl 5-(Cbz-amino)-4-oxopentanoate This compound was prepared from the product of 15a (1.2 g; 3.2 mmol), 5-(Cbz-amino)-4-oxopentanoic acid (0.84 g; 3.2 mmol), 4-pyrrolidinylpyridine (50 mg), and N,N'-diisopropylcarbodiimide (0.50 g; 4.0 mmol) in dichloromethane (35 mL) according to Procedure D. The reaction time was 3 days. The crude product was purified on a 85×55 mm silica gel 60 column eluted with ethyl acetate-hexane (1:1) (1000 mL) collecting 13×50 mL fractions. Fractions containing the product (3-6) were evaporated and 0.57 g (29%) product was obtained (white solid, mp 78-81° C.).

$^1$H NMR (200 MHz; DMSO-$d_6$): δ 1.24 (22H, br s), 1.54 (4H, br s), 2.33 (2H, t, J=7.4 Hz), 2.48 (2H, br s), 2.68 (2H, br s), 3.88 (2H, br s), 3.98 (2H, br s), 5.04 (2H, s), 5.08 (2H, s), 7.34 (10H, s) ppm.

$^{13}$C NMR (50 MHz; DMSO-$d_6$): δ 24.4, 25.3, 27.4, 28.1, 28.3, 28.6, 28.9, 33.5, 33.8, 49.8, 63.9, 65.2, 65.5, 127.4, 127.6, 127.7, 128.1, 128.2, 136.9, 171.8, 205.2 ppm.

15c—Preparation of 15-carboxypentadecyl 5-amino-4-oxopentanoate hydrochloride

This compound was prepared from the product of 15b (0.45 g; 0.74 mmol), 12 M HCl (0.062 mL; 0.74 mmol), 10% Pd/C (100 mg), hydrogen gas, and 2-propanol (25 mL) using the procedure in Example 8d. 0.06 g (19%) product was obtained (white solid).

$^1$H NMR (200 MHz; DMSO-$d_6$): δ 1.1-1.7 (28H, m), 2.25 (2H, m), 2.52 (2H, m), 2.82 (2H, m), 3.9-4.1 (4H, m), 8.43 (3H, s), 12.1 (1H, br s) ppm.

$^{13}$C NMR (50 MHz; DMSO-$d_6$): δ 24.4, 25.3, 27.0, 27.2, 27.6, 28.0, 28.4, 28.6, 28.9, 33.6, 34.2, 46.4, 63.9, 171.8, 174.1, 202.3 ppm.

EXAMPLE 16

In Vivo Skin Fluorescence Study in Healthy Nude Mice

A study was carried out to assess the potential of the compounds of the invention as precursors for photosensitisers for skin application. As such, the compounds of the invention need to be able to penetrate the skin, to be taken up by the cells in the skin and to be converted to photosensitisers. The result of this process can be visualized by exposing the skin to light which excites the photosensitiser molecules and to determine the amount of energy which is released in the form of fluorescence when the excited photosensitiser molecules relax to an energetically lower state.

The following compounds of the invention were tested on the skin of healthy nude mice:

Compound 2: 1-(isopropyl carboxy)ethyl 5-amino-4-oxopentanoate hydrochloride (prepared according to Example 2)

Compound 4: 2-carboxyethyl 5-amino-4-oxopentanoate hydrobromide (prepared according to Example 4)

Compound 7: (4-carboxyphenyl)methyl 5-amino-4-oxopentanoate hydrobromide (prepared according to Example 7)

Compounds 2, 4 and 7 above were formulated as creams in Unguentum Merck. The compounds were tested in equimolar amounts:

16% (160 mg/g) compound 2
16% (160 mg/g) compound 4; and
19% (190 mg/g) compound 7.

3 groups of mice (5 mice/group, each mouse of one group receiving the same cream formulation) were included in the experiment. About 100 µl of cream formulation was applied onto the back of one mouse. The mice were kept in the dark for 6 hours prior to skin fluorescence measurement to avoid photobleaching. For assessment of skin fluorescence, a fluorescence camera (Medeikonos PDD/PDT, Medeikonos AB, Gothenburg, Sweden) was used and images of the back of each mouse were taken. Excitation was carried out at wavelengths of 365 and 405 nm and 2 s illumination time. Each image was calibrated to a fluorescence standard (Uranyl Standard, J&M, Analytische Mess- and Regeltechnik GmbH, Hamburg, Germany) and adjusted for background fluorescence. The mean amount of skin fluorescence in each image was calculated by means of image analyzer-software (Mat-Lab 7.2.0.232, Math-Works, Natick, Mass., USA) and the mean amount of skin fluorescence for each group of mice (5 mice/compound) was calculated.

Results:

| Compound | Skin fluorescence [a.u.] |
|---|---|
| 2 | 31557 |
| 4 | 8473 |
| 7 | 2995 |

All 3 tested compounds resulted in skin fluorescence with compound 2, 1-(isopropyl carboxy)ethyl 5-amino-4-oxopentanoate hydrochloride, showing the highest level of fluorescence.

EXAMPLE 17

In Vivo Skin Fluorescence Study in Minipigs

Compound 1c (carboxymethyl 5-amino-4-oxopentanoate hydrobromide, prepared according to Example 1c) was formulated as a cream in Unguentum Merck (15%, 150 mg/g; 0.56 mmol).

The cream was administered to the back skin of minipigs. Prior to application of the cream, the surrounding skin was cleaned with sterile water and gauze, if necessary. 0.5 g cream was applied to each test site (50 mm in diameter) resulting in a homogenous cream layer and then covered with a dressing (Tegaderm®). The gauze Vet-Flex® was used to keep the dressing in place.

Skin fluorescence at 630 nm was assessed prior to cream application and at 1.5, 5 and 12 hours after cream application using the FluoDerm instrument (DiaMedico ApS, Denmark) according to the manufacturers instructions. The FluoDerm instrument is a hand-held device for objective real-time in vivo measuring of average fluorescence over a circular field with diameter 40 mm. Measurements were electronically corrected for the actual ambient light. The results are shown in FIG. 1.

Results:

It can be seen from FIG. 1 that the skin fluorescence increased with time.

Skin Biopsies:

The cream was administered as described above. At t=0 (i.e. prior to administration of the cream), 1.5, 5 and 12 hours, biopsy samples were taken using a 10 mm biopsy punch (AcuPunch 10 mm, Acuderm, USA). The samples were taken and handled in a minimally illuminated room. Each sample was trimmed free of any subcutaneous fatty tissue and thereafter cut in half. Each sample was then snap frozen in liquid nitrogen, in an aluminium foil bag or similar, and transferred to a −80° C. freezer.

The biopsy samples were sectioned at 10 µm and again care was taken to minimize the surrounding light. When sebaceous glands and epidermis could be identified, a series of 3 consecutive sections was prepared from each sample. The sections were examined within 15 minutes in a Leica DMRXE microscope equipped for both ordinary light microscopy and fluorescence microscopy. Epidermis and sebaceous glands were localized using conventional light microscopy. This was carried out within 5 seconds and then the light source was changed to a mercury lamp/fluorescence with filter set; excitation filter 390-447 nm, beam splitter 455 nm and an emission filter >600 nm. The sections were immediately photographed. Without moving the specimen the light source was changed back to conventional light microscopy and the sections were photographed in exactly the same position as for the fluorescence microscopy. As well as the epidermis and sebaceous glands, the dermis was analysed and if fluorescence was found also photographed. To further investigate localisation of all analyzed structures, the sections were stained with hematoxylin/eosin.

Image analysis was performed using the software program, Image J (version Fiji-win32.exe). With this program, average fluorescence intensity per pixel was measured from the saved images.

Results:

After 1.5 hours, fluorescence could already be seen in the sebaceous glands, and after 5 hours, fluorescence was also seen in the epidermis. Compound 1c thus shows a selectivity for sebaceous glands and hence may be useful for the photodynamic treatment of diseases affecting the sebaceous glands, such as acne, keratosis pilaris, sebaceous hyperplasia, sebaceous gland carcinoma or sebaceous adenoma.

EXAMPLE 18

In Vivo Skin Fluorescence Study in Healthy Nude Mice and Nude Mice with UV-Damaged Skin An experiment was carried out to assess the potential for compound 6 to show selective accumulation in UV-damaged skin. For the assessment, skin fluorescence after application of the compound was measured in vivo in healthy mouse skin and in UV-damaged mouse skin. A nude mice model with UV-damaged skin (actinic damage) was established as described by K. Togsverd-Bo et al., Exp. Dermatol. 2012, 21, 260-264.

Equimolar amounts of compound 2 (1-(isopropyl carboxy) ethyl 5-amino-4-oxopentanoate hydrochloride prepared according to Example 2) and compound 5 (3-carboxypropyl 5 amino-4-oxopentanoate hydrochloride prepared according to Example 5) were formulated as a cream in Unguentum Merck: compound 2: 16%, 160 mg/g and compound 5: 14%, 140 mg/g, respectively.

One group of healthy nude mice (10 mice, control group) and one group of nude mice with UV-damaged skin (10 mice) were included in the experiment. About 125 µl of cream formulation was applied onto the back of each mouse. Prior to cream application, the dorsal skin of each mouse was tape-stripped five times to enhance penetration of the compound: adhesive film (Scotch tape, 3M) was pressed onto the skin of the application area, the tape strip was removed with one quick movement and a new tape strip was used. The mice were kept in the dark for 3 hours prior to skin fluorescence measurement to avoid photobleaching. Skin fluorescence was assessed as described in Example 17 and the mean amount of skin fluorescence for each group of mice was calculated.

Results:

The ratio of skin fluorescence [a.u] in UV-damaged mouse skin to skin fluorescence [a.u.] in healthy mouse skin was determined.

The ratio for compound 2 was 1.14 while the ratio for compound 5 was 2.72. Hence compound 2 shows some selectivity for UV-damaged skin while compound 5 shows a pronounced selectivity for UV-damaged skin.

EXAMPLE 19

PDT Efficacy in Bacteria

The efficacy of various compounds according to the invention to kill bacteria via a photodynamic reaction was investigated in the Gram positive bacterium *Staphylococcus aureus*.

The following compounds of the invention were tested:
Compound 1c: carboxymethyl 5-amino-4-oxopentanoate hydrobromide (prepared according to Example 1c)
Compound 4: 2-carboxyethyl 5-amino-4-oxopentanoate hydrobromide (prepared according to Example 4)

Bacterial Strain:

*S. aureus* strain DSM 20231 (ATCC 12600). The bacterial strain was grown for 24 hours on heart infusion agar (Difco) at 35-37° C. prior to carrying out the experiment and re-suspended in 20 mM PIPES, pH 7.2-7.4 at a concentration corresponding to a McFarland 0.5 standard (approximately $1\text{-}5 \times 10^8$ CFU/mL). In order to ensure viable cell cultures and to check the inoculum size and purity, bacterial stocks were made immediately prior to experimentation and the CFU/mL determined in a standard colony assay.

Dark-Toxicity:

"Dark toxicity", i.e. the toxic effect of the compounds in the absence of light (and therefore unrelated to PDT effects), can include bacteria cell death and therefore can interfere with the accurate measurement of the PDT effect, which also results in bacterial cell death. Dark toxicity can be measured by determining the toxicity of each compound under the same experimental conditions, but in the absence of light, thereby avoiding any PDT effect. The use of the compounds of the invention under conditions that produce low dark toxicity is advantageous because dark toxicity effects could also include harming or killing non-target cells and interfering with the PDT treatment itself. In view of these considerations, an optimal agent for use in PDT-mediated killing of bacteria cells should display both a low dark toxicity and a high potency to induce a photodynamic effect so as to kill the target bacterial cells.

Dark toxicity was determined as described in the paragraph "PDT-treatment" below, except that the plate was not illuminated. Subsequently, a microplate assay was carried out as described below.

The dark toxicity of compounds 1c and 4 was tested at concentrations of 0.001, 0.1, 1 and 10 mM. No dark toxicity was observed at any of these concentrations.

PDT-Treatment:

Stock solutions of compounds 1c and 4 were made in DMSO at 100 mM. Prior to the experiment, 0.02 mL of DMSO (control) or stock solution of compounds 2 and 3 were pipetted into wells of VisiPlates-24 to obtain concentrations of 0.01 mM, 0.1 mM and 1 mM. To each well was added 2 mL of the bacterial stock culture followed by mixing using an automatic pipette. All wells contained a final concentration of 1% DMSO. After 4 hour incubation the plate was illuminated with red light (Aktilite® CL128 lamp) for 32 minutes (light dose 148 J/cm$^2$). In order to achieve an even illumination of all the wells the plate was illuminated from below (flat bottom wells) whilst a small circular motion within the field of the lamp was applied.

Microplate Assay:

After illumination the entire well contents were transferred to Eppendorf tubes, and 0.1 mL of the contents was re-introduced into wells of a microplate. To the re-introduced inoculum was added 1.5 mL of heart infusion broth (Difco) for the generation of growth curves. All transfers were proceeded by a thorough mixing of the contents by pipetting.

Plates were incubated at 37±1° C. by applying the temperature function of a Victor 1420 Multilabel Counter (Perkin Elmer, Turku, Finland). Growth curves were generated by measurement of the absorbance at 595 nm at regular intervals until the bacteria cells had entered the logarithmic phase of growth. Measurements were made automatically by the Multilabel Counter.

The raw data were plotted on semi-logarithmic axes (log 10 absorbance against time (1 unit=15 min)) to determine the time after inoculation at which bacteria cells enter the logarithmic phase of growth (i.e. the length of the lag phase). The length of the lag phase depends on the number of surviving cells and increases proportionally to the efficacy of the photodynamic treatment.

Results:

The results are shown in FIG. 2 from which it can be seen that both compounds were effective in killing S. aureus bacteria and were able to effectively delay the re-growth of the bacteria cells.

EXAMPLE 20

Ames Test

The Ames test (see B. N. Ames et al, Methods for detecting carcinogens and mutagens with the Salmonella/mammalian-microsome mutagenicity test. Mutation Research 31, 347-364, 1975) is a standard test method approved by the regulatory authorities to detect an ability of a test chemical compound to induce mutation in certain bacterial strains. If a test chemical compound induces such mutations, it cannot be used in a pharmaceutical compound for use in humans.

The objective of this study was to evaluate the mutagenic potential and photomutagenic potential of compound 1c, carboxymethyl 5-amino-4-oxopentanoate hydrobromide (prepared according to Example 1c) by examining its ability to revert two histidine-requiring strains of Salmonella typhimurium, TA98 and TA100, in the absence and presence of a rat liver metabolising system (S-9) and also in the absence and presence of visible light. The latter was assessed since compound 1c is taken up by the bacteria cells and converted into a photosensitiser, which, upon illumination of said cells, might induce mutagenic products.

The results show that compound 1c did not induce mutation or photomutation in those two strains of Salmonella typhimurium, when tested under the conditions employed for this study.

EXAMPLE 21

In Vitro PpIX Fluorescence Study in Cancer Cells

A study was carried out to assess the potential of the compounds of the invention as precursors for photosensitisers. As such, the compounds of the invention need to be taken up by the cells and need to be converted to photosensitisers, i.e. PpIX. The result of this process can be visualized by exposing the cells to light which excites the PpIX molecules and to determine the amount of energy which is released in the form of fluorescence when the excited PpIX molecules relax to an energetically lower state.

The following compounds of the invention were tested:
Compound 5 (3-carboxypropyl 5 amino-4-oxopentanoate hydrochloride prepared according to Example 5)
Compound 9 (5-carboxypentyl 5-amino4-oxopentanoate hydrochloride prepared according to Example 9)
Compound 10 (7-carboxyheptyl 5-amino4-oxopentanoate hydrochloride prepared according to Example 10)
Compound 12 (9-carboxynonyl 5-amino4-oxopentanoate hydrochloride prepared according to Example 12)
Compound 14 (11-carboxyundecyl 5-amino4-oxopentanoate hydrochloride prepared according to Example 14)
Compound 15 (15-carboxypentadecyl 5-amino4-oxopentanoate hydrochloride prepared according to Example 15)

The following compounds were used as reference compounds:
5-ALA hydrochloride (ALA)
5-ALA hexyl ester hydrochloride (HAL)

Stock solutions of the compounds above were prepared by dissolving them in DMSO to a concentration of 100 mM. Concentrations used in the experiments were obtained by diluting the stock solutions with PBS or cell culture medium.

Cell Cultivation and Treatment of Cells with Compounds and References:

WiDr cells derived from a primary adenocarcinoma of the rectosigmoid colon were subcultured in RPMI 1640 medium (Gibco) containing 10% fetal calf serum, 100 U/ml penicillin, 100 µg/ml streptomycin and 1% glutamine. Cells were split 1:100 twice a week, and maintained at 37° C. and 5% $CO_2$ in a humid environment. For carrying out the experiments, $5\times10^5$ WiDr cells in 2 ml of the medium described above were added to each well of 6-well plastic tissue-culture plates (Nunc) and left for 48 hr at 37° C. and 5% $CO_2$ in a humid environment for proper attachment to the substrate. The cells were then washed twice with RPMI 1640-medium without serum, followed by the addition to the wells of the appropriate dilutions of the compounds and references above in 2 ml of fresh culture medium to final concentrations of 0.001, 0.003, 0.01, 0.03, 0.1, 0.3 and 1 mM in duplicates. To two wells, only 2 ml of fresh culture medium was added. These untreated cells served as a control. The cells were incubated at 37° C. for four hours in the dark.

Dark Toxicity:

Dark toxicity, i.e. cell toxicity in the absence of light, was measured by MTS assay immediately after the above-described 4 hours of incubation with the compounds and references at various concentrations. For ALA hydrochloride and compounds 5, 9, 10, 12 and 14 no cell toxicity was observed for any of the tested concentrations. For hexyl ester hydrochloride, a weak cell toxicity was observed in the range of 0.3 to 1 mM with a minimum cell survival rate of 85%. Compound 15 was toxic in concentrations above 0.1 mM.

PpIX Formation:

After treatment with the compounds of the invention and reference compounds as described above, the cells were washed twice with PBS and scraped off the substrate with a Costar cell scraper into a solution of 1M $HClO_4$ in 50% methanol. Cell debris was removed by centrifugation. PpIX was quantitatively extracted from the cells with this procedure. The PpIX content in each sample was determined fluorometrically using a Perkin Elmer LS50B spectrofluorimeter. PpIX was excited at 407 nm, and the emitted fluorescence was measured at 606 nm using a long pass cut-off filter (530 nm) on the emission side. A standard of known PpIX concentration was added to the samples at concentrations increasing the total fluorescence by 50-100%. The PpIX concentration in each sample was calculated relative to the protein content in control cells as measured by a bicinchoninic acid protein assay.

Results of PpIX Formation:

| Compound | Max. PpIX content [ng/mg protein] | Compound concentration for max PpIX formation [mM] |
| --- | --- | --- |
| ALA | 80* | ≥1 |
| HAL | 94** | 0.1 |
| Compound 5 | 30 | 1 |
| Compound 9 | 40 | 1 |
| Compound 10 | 55* | 1 |
| Compound 12 | 90* | 0.05 |
| Compound 14 | 65* | 0.1 |
| Compound 15 | 25 | 0.1 |

*mean of two experiments;
**mean of 3 experiments

The results show that all tested compounds are useful photosensitising agents in cancer cells, i.e. have a potential to be used in the photodynamic treatment of cancer: all tested compounds are converted to PpIX in cancer cells and concentrations at which a maximum of PpIX is formed are not toxic to the cells, i.e. there is no dark toxicity observed at such concentrations. There is a trend that the maximum PpIX concentration tends to occur at lower concentrations for the longer-chained compounds.

EXAMPLE 22

In Vitro PpIX Fluorescence Study in Rat Bladder Cells

5-ALA hexyl ester hydrochloride (HAL) is the active ingredient of Hexvix®, a commercially available drug for the photodynamic detection of cancer in the bladder. Investigational studies also show the use of Hexvix® for the photodynamic treatment of bladder cancer. HAL is converted to PpIX in bladder cancer cells and can be detected by its characteristic fluorescence. Early studies in the development of Hexvix® were carried out in rat bladder cells and tissue as a model for human bladder cells and tissue. This study was carried out as a first step to assess the potential of the compounds of the invention as precursors for photosensitisers which can be used in the bladder. In such a first step, the appropriate concentration for the compounds is established in vitro by comparing the PpIX fluorescence of the compounds to those of HAL. Based on the results, the concentration for a future in vivo study is established.

The following compounds were tested:

Compound 4: 2-carboxyethyl 5-amino-4-oxopentanoate hydrobromide (prepared according to Example 4)

Compound 5: (3-carboxypropyl 5-amino-4-oxopentanoate hydrochloride prepared according to Example 5)

Compound 8: 2-carboxybutyl 5-amino-4-oxopentanoate hydrochloride prepared according to Example 8)

5-ALA hexyl ester hydrochloride (HAL) was used as a reference compound.

PpIX Measurements in Rat Bladder Cells:

Rat bladder cells (AY-27) were grown in the culture medium (RPMI 1640 supplemented with 9% fetal calf serum 1% L-glutamin (200 mM) and 1% penicillin (10 000 UI), streptomycin (10 000 µg·mL$^{-1}$). Exponentially growing cells (AY-27) were incubated for 2 hours with freshly prepared solutions of 0.8 mM HAL (which is a tenth of the concentration which is used for bladder cancer detection in human patients) and freshly prepared solutions of compounds 4, 5 and 8 at concentrations of 3-15 mM (see table below). Control cells received serum-free medium without any test or reference compounds. After the incubation, the solutions or the medium was discarded and the cells were rinsed 2 times with ice-cooled PBS. PpIX was extracted from cells using an ice-cold lysis extraction mixture, consisting of ethanol/DMSO/acetic acid (80/20/1, v/v/v). The cell lysate was centrifuged (400 g, 10 min, 2° C.), the pellet was grinded and the suspension was sonicated for 15 min before being centrifuged. The fluorescence signal of PpIX was measured with a Perkin-Elmer LS 55 spectrometer (Perkin-Elmer, Beaconsfield, UK) and expressed as a function of the protein content. The fluorescence intensity at 635 nm in each sample was reported on a calibration curve established with PpIX (Sigma-Aldrich, France) diluted in extraction mixture as described above. The PpIX concentration was expressed relative to the protein content. Briefly, a lysis buffer mixture (1 mM EDTA, 1% Triton X-100 and 10 mM Tris-HCl; pH 7.4) was added to frozen cell dishes together with 500 mM PMSF (anti-protease) solution in DMSO. Lysates were kept on ice for 30 minutes and centrifuged at 4° C. for 20 minutes at 15 000 g. The protein content was then measured against a BSA calibration curve by a Biorad DC protein assay kit (Bio-Rad, France) based on a method developed by Lowry.

All experiments were performed in 4-5 replicates under subdued light. For concentrations of compounds 1 mM, the cytotoxicity was assessed with MTT test. Exponentially growing cells were incubated with freshly prepared solution or medium as described above for 2 hours in 96-well plates. After the incubation, the solutions or the medium was discarded and the cells were washed twice with PBS. Then 50 µl of MTT (2.5 mg·ml$^{-1}$) was added to 150 µl of RPMI serum-free medium per well and incubated for 3 hours. Absorbance was measured by dissolving formazan crystals with 50 µl of DMSO. The absorbance was normalized to that of control cells.

| Compound | Concentration (mM) | PpIX (pmoles/mg protein) Mean ± SD | Cytotoxicity (% of control) |
|---|---|---|---|
| HAL | 0.8 | 304 ± 65 | 15 |
| Compound 4 | 1 | 45 ± 8 | 3 |
|  | 5 | 141 ± 24 | 14 |
|  | 15 | 180 ± 94 | 39 |
| Compound 5 | 0.3 | 221 ± 32 | N/A |
|  | 0.5 | 224 ± 35 | N/A |
|  | 1 | 261 ± 52 | 17 |
|  | 5 | 250 ± 83 | 30 |
|  | 15 | 216 ± 11 | 37 |
| Compound 8 | 0.3 | 243 ± 28 | N/A |
|  | 0.5 | 219 ± 51 | N/A |
|  | 1 | 258 ± 62 | 18 |
|  | 5 | 234 ± 78 | 26 |
|  | 15 | 213 ± 64 | 38 |

It can be seen from the table that HAL, which was used as a reference, generated about 304 pmole PpIX/mg protein with an acceptable cytotoxicity level of 15%.

Compound 4 induced PpIX concentrations that were significantly lower compared to HAL at about the same concentration (1 mM). About half of the PpIX concentration of HAL was obtained with about 6 times the concentration (i.e. 5 mM). At higher concentration, cytotoxicity was induced.

Compounds 5 and 8 induced PpIX concentrations that were similar to that of HAL at comparable concentrations (i.e. 1 mM) and at 5 mM. The levels of cytotoxicity were also comparable and acceptable at 1 mM. Hence compounds 5 and 8 are promising candidates for use as precursors of photosensitisers in PDD and PDT in the bladder.

pH Experiments:

The bladder is sensitive to low pH while the compounds of the invention (and ALA-esters generally) form pyrazines at higher pH. Hence a solution of the compounds of the invention must not result in a pH which is not tolerable for the bladder. The effect of the test compounds on pH in the medium was tested by adding the compounds at 1, 5 and 25 mM to RPMI 1640 medium followed by measurement of pH. It was found that the compounds at 1 mM did not change the pH in the medium while the compounds at 5 and 25 mM changed the pH from 7.5 to 7.1 and 5.5, respectively. By plotting the data it was found by interpolation that the compounds at 15 mM would result in pH 6.0. Below pH 6, adverse effects in the bladder (contractions etc.) may occur. 15 mM is well above the 10 mM anticipated concentration for in vivo studies (based on the experiences with HAL and the assumption that 10-times the in vitro concentration will be used in vivo).

The invention claimed is:

1. A compound of general formula I, or a pharmaceutically acceptable salt thereof:

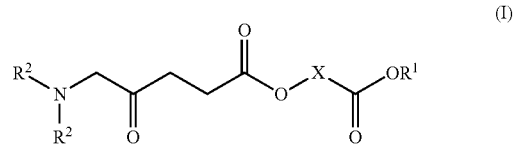

(I)

wherein $R^1$ represents a hydrogen atom or an optionally substituted alkyl or cycloalkyl group;

$R^2$, each of which may be the same or different, represents a hydrogen atom or an optionally substituted alkyl group; and X is a straight-chained or branched alkylene group, a cycloalkylene, arylene, or aralkylene group each of which may optionally be substituted by one or more non-hydrophilic substituents.

2. A compound as claimed in claim 1, wherein $R^1$ is hydrogen or a short, straight-chained or branched alkylene group.

3. A compound as claimed in claim 1, wherein group X is an optionally substituted, straight-chained $C_{1-4}$ alkylene group, an optionally substituted branched $C_{2-6}$ alkylene group, an optionally substituted $C_{5-6}$ cycloalkylene group, an optionally substituted $C_{6-12}$ arylene group, or an optionally substituted $C_{7-15}$ aralkylene group.

4. A compound as claimed in claim 3, wherein group X is an unsubstituted straight-chained $C_{1-4}$ alkylene group, an unsubstituted branched $C_{2-6}$ alkylene group, or a straight-chained $C_{1-2}$ alkylene group substituted by one or more halo or aryl groups.

5. A compound as claimed in claim 1, wherein each $R^2$ represents hydrogen.

6. A compound as claimed in claim 1 which is a compound selected from any of the following, or a pharmaceutically acceptable salt thereof:

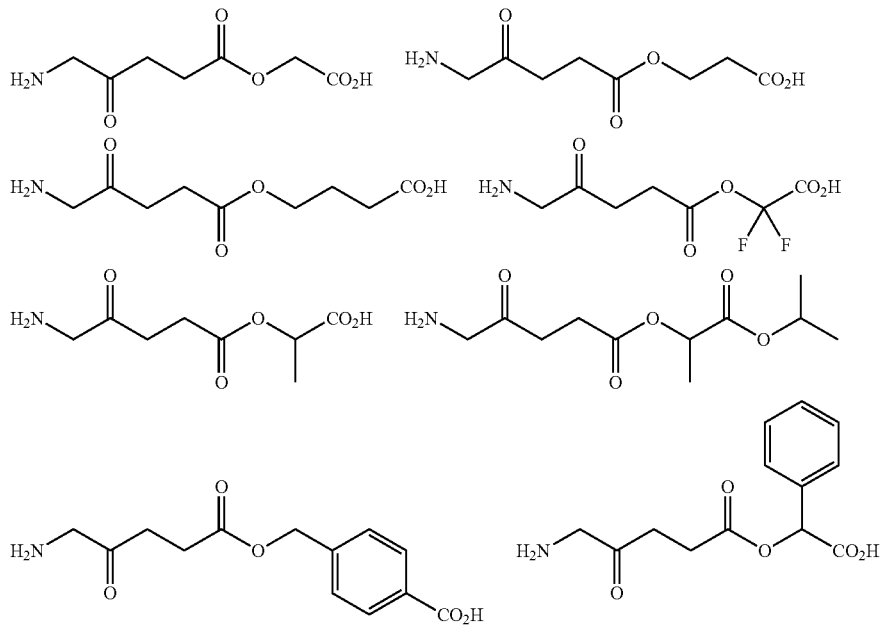

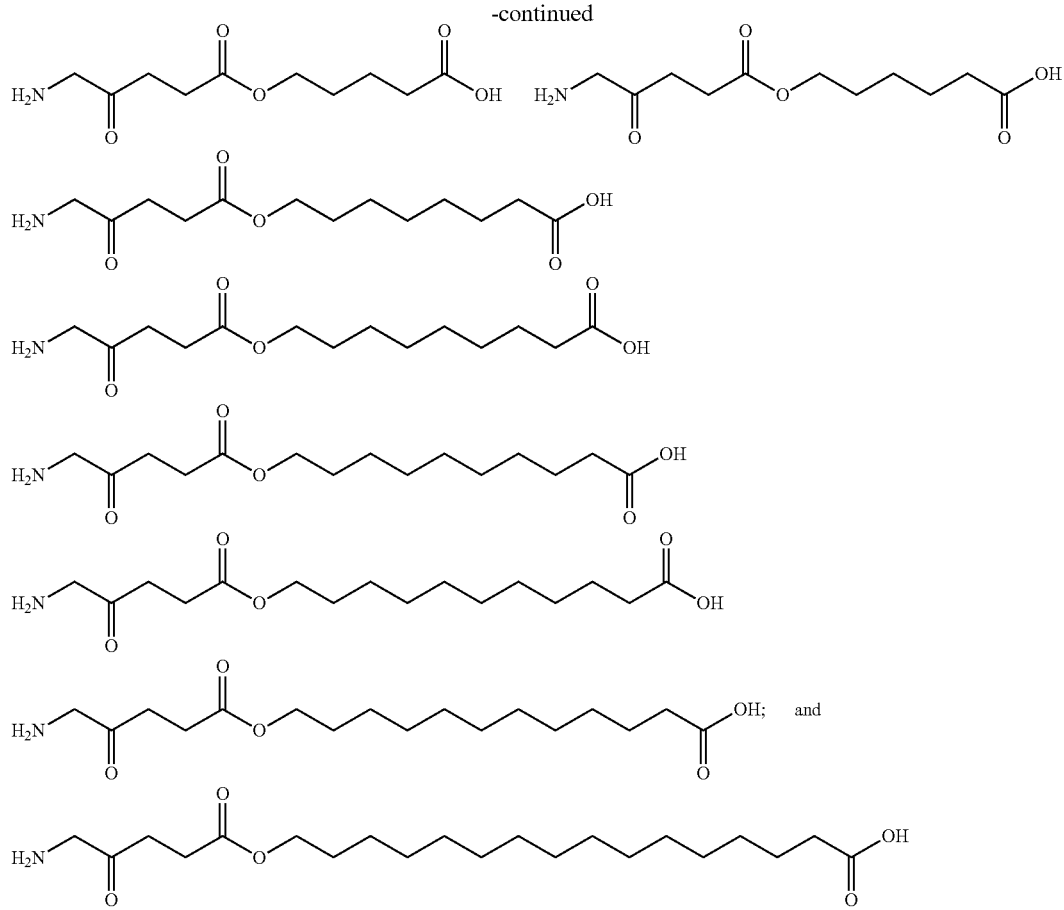

7. A composition comprising a compound of formula I, or a pharmaceutically acceptable salt thereof, as claimed in claim 1, together with at least one pharmaceutically acceptable or cosmetically acceptable carrier or excipient.

8. A compound as claimed in claim 1 for use in a method of photodynamic treatment or diagnosis.

9. A compound for use as claimed in claim 8, wherein said method is for the treatment or diagnosis of cancer; an infection associated with cancer; a viral, bacterial or fungal infection; or a non-cancerous condition.

10. A compound as claimed in claim 1, wherein the one or more non-hydrophilic substituents are selected from halo, nitro and aryl, wherein the aryl is optionally substituted by one or more halo, alkyl, haloalkyl, alkoxy or nitro groups.

11. A compound as claimed in claim 2, wherein $R^1$ is methyl, ethyl, n-propyl or isopropyl.

12. A compound as claimed in claim 8, wherein the method of photodynamic treatment or diagnosis is for the treatment or diagnosis of a disorder or abnormality of an external or internal surface of the body which is responsive to photodynamic treatment or diagnosis.

13. A compound for use as claimed in claim 9, wherein the cancer is bladder cancer, colon cancer or stomach cancer; the infection associated with cancer is a viral infection; the viral, bacterial or fungal infection is *Helicobacter pylori* infection or acne; and the non-cancerous condition is inflammation.

14. A compound for use as claimed in claim 13, wherein the viral infection is an infection caused by human papilloma virus, hepatitis B or Epstein Barr virus.

15. A compound for use as claimed in claim 14, wherein the inflammation is inflammatory acne, colitis or infective dermatitis.

16. A compound as claimed in claim 1 wherein X is a straight-chained alkylene group which consists of 1 to 16 carbon atoms.

17. A compound as claimed in claim 16 wherein X is methylene, ethylene, propylene, butylene, pentylene, hexylene, heptylene, octylene, nonylene, decylene, undecylene, dodecylene, tridecylene, tetradecylene, pentadecylene or hexadecylene.

18. A compound as claimed in claim 1 wherein X is a straight-chained alkylene group which consists of 1 to 6 carbon atoms.

19. A compound as claimed in claim 18 wherein X is methylene, ethylene, propylene, butylene, pentylene or hexylene.

* * * * *